(12) United States Patent
Hampson et al.

(10) Patent No.: US 7,531,176 B2
(45) Date of Patent: May 12, 2009

(54) BRACHYSPIRA PILOSICOLI 72 KDA OUTER-MEMBRANE PROTEIN AND DIAGNOSTIC AND THERAPEUTIC USES THEREOF

(76) Inventors: David J Hampson, 28 Haslemere Drive, Mt. Nasura (AU) 6112; Tom La, 248 William Street, Beckenham (AU) 6107

( * ) Notice: Subject to any disclaimer, the term of this patent is extended or adjusted under 35 U.S.C. 154(b) by 0 days.

(21) Appl. No.: 10/583,202

(22) PCT Filed: Dec. 17, 2004

(86) PCT No.: PCT/AU2004/001783

§ 371 (c)(1),
(2), (4) Date: Jun. 16, 2006

(87) PCT Pub. No.: WO2005/059137

PCT Pub. Date: Jun. 30, 2005

(65) Prior Publication Data

US 2007/0026017 A1    Feb. 1, 2007

(30) Foreign Application Priority Data

Dec. 19, 2003   (AU) .............................. 2003907017

(51) Int. Cl.
*A61K 39/02*     (2006.01)
*C07K 14/195*    (2006.01)

(52) U.S. Cl. .................. 424/190.1; 424/234.1; 514/12; 530/30; 530/825

(58) Field of Classification Search ....................... None
See application file for complete search history.

(56) References Cited

OTHER PUBLICATIONS

Trott et al. The search for *Brachyspira* outer membrane proteins that interact with the host. Animal Health Research Reviews. 2001, vol. 2, No. 1, pp. 19-30.*
Medline Abstract 9568997 & Tenaya et al.: "Preparation of diagnostic polyclonal and monoclonal antibodies against outer envelope proteins of *Serpulina pilosicoli*", J. Med. Microbiol. vol. 47, No. 4, 1998, pp. 317-324.
Medline Abstract. 10659358 & Zhang, P. et al.: "Recovery from colonic infection elicits serum IgG antibodies to specific *Serpulina pilosicoli* outer membrane antigens (SPOMA)." Adv. Exp. Med. Biol. vol. 473, 1999, pp. 191-197.
Genbank Accession No. AE002369 Tettelin, H. et al.: "*Neisseria meningitidis* SerogroupB strain MC58." May 25, 2000.

* cited by examiner

*Primary Examiner*—Jeffrey E Russel
(74) *Attorney, Agent, or Firm*—Christensen O'Connor Johnson Kindness PLLC

(57) ABSTRACT

The invention relates to *Brachyspira pilosicoli* 72 kDa outer-membrane protein (Bpmp-72) and its amino acid and nucleotide sequence. The invention also relates to the uses of these sequences in prophylactic (vaccination) and therapeutic treatment of infections with *Brachyspira pilosicoli* (internal spirochaetosis).

8 Claims, 13 Drawing Sheets

```
 -101   AGCGTTTAGC TGAACTTGAA GCTATGGTAA AAGAGCTTGA AACTTTAGAG
                                                -35
  -51   CAAGAGCAAC AAAGCTAATA TTTTAATATT TTAAGGAGTA TAAAAGAAAA
                                    -10         SD
    1   ATGAGTACTT TAATAAAGAA AATCGTAGCT TATATAGCTT TAATCTCTTT
   51   TAGTTTTAGC GTATTACCTG CTCAAACTTA TGATGATGCG GCTAGAATTA
  101   CTGGAGAAGC TGAGACTTTA CAAATGACG GAGAATACCA AAAGTCTTAT
  151   GATAAATCTC AAGAGGCTTC TGACTCTATA GATAAACTA CTGTATCATT
  201   ATTTTATAGA TTAATGAACT TAAGAATAGC TAAAGCAAAA AATGATGCAA
  251   ATAAGACTAT TAATGAAATA GAACAATTAG GTGCTTCTAC TGATAATGAA
  301   TTTAAAACAA ATATCAAGA AGCTCTAAAA TTCTTTGAAG AAGGAAATAA
  351   TAGTATTACT AACTTACCTC CAGAACCGCA AACTCCTCCT ACAGATGAAG
  401   AGTTTACTGC TTCTTCAAAC ACATTCACTA CAGTATATAA TTCTTTCAAC
  451   AATGCTTTAC AATCTGCTAA CAGTGTAAAA GAAGGTTATC TTAATAGAGA
  501   AAGAGCAATA GCTTCAAAAT CCATTAATGA TGCTAGAAAC AAATATAAAG
  551   CAGAATTAGG CAAGAGTGTA AAAGCAGGCG ATGCTAATGA TAGAAATATT
  601   AATGGTGCTT TAACTAGAGC TGATGAAGCA CTTAGCAATG ACAATTTTGC
  651   AAGCGTTCAG CAGAATGTAT CTACTGCATT AGCTGGTATA ATAAAGCTA
  701   TAGCAGATGC TAAGGCGAAA GCTGAGGCAG AAGCTAAAGC AAAAGCTGCT
  751   GCTGAAGCTA AGGCAAGAGC TGAAGCAGAG GCTAAAGCGA AGCAGAAGC
  801   TGCTGCTAAA GCAAAAGCTG AAGCAGAGGC TAAAGCGAAA GCAGATGCAA
  851   TAGCAAAAGC TAAAAAAGAC ATAGAAGATG CACAAAATAA ATATAATAAT
  901   TTAGTTAATG ATCAAGTAAT AGCTAAAGGT GATGATAATG ATAAAAACGT
  951   ATCAAAACTT TTAACTGATG CTAATAATGC TTTACAAAAC ACTCCTCAAA
 1001   CTGCAAGCGA TAAAGCTTTA GAAGCTTCTA AAACTATGGA TAATATATTA
 1051   AACACTGCTA ATCAATTGAA AAAGAAGAA GCTGTTAAAA ATCTAGAGCA
 1101   ATTAAAGGCA AGAAGAGACA GACTTATAAG CGAAGGTTAT TTAACTAAAG
 1151   ACAGCGAAGA AGAACAAAAG TTATCTCAAA CTATTAAAGA AGCTGAAGAT
 1201   GCTTTAAATA ACAATGATTA TGTTTTAGCT GACCAAAAAA TGCAGGAAGC
 1251   TAATCTTAAC ATGAATGCTA TAGAAGAGAG AGGACCTATT GACGGACAAG
 1301   TTATACCTGG TGAAATGGGC GGTAACGAAA CTGGTCAAAT AATTGATGCT
 1351   ACTACTGGTC AAGAAGTAAA TACAGAAGGA AAAGTTACTG TATTACCTCA
 1401   ATATTATGTT GTAGTAAGAA GAGTACCTCT AACTGATGCT TTATGGAGAA
 1451   TTGCTGGATA CAGCTACATA TACAACAACC CTATAGAATG GTACAGAATA
 1501   TATGAAGCTA ACAGAAATGT ACTTAGAGAC CCTAATAACC CTGATTTAAT
 1551   ACTTCCTGGT CAAAGATTAA TAATACCTAG CCTTAATGGT GAAGAGAGAA
 1601   GCGGTGATTA TAATCCTGAT TTAGAGTATT TGACTTATGA TGAGGTTATG
 1651   CAGTTAAGAC AGCAAAATAA CACTACTCAA GCACAACAGT AAGAAATAAA
 1701   CTTATAAAAT ACAAAAGGTC ATGCATTTAA TATGTATGAC CTTTTTTTGT
```

FIGURE 3

SEQUENCE LISTING

<160> NUMBER OF SEQ ID NOS: 38

<210> SEQ ID NO 1
<211> LENGTH: 1750
<212> TYPE: DNA
<213> ORGANISM: Brachyspira pilosicoli

<400> SEQUENCE: 1

```
atgagtactt taataaagaa aatcgtagct tatatagctt taatctcttt tagttttagc    60
gtattacctg ctcaaactta tgatgatgcg gctagaatta ctggagaagc tgagacttta   120
caaaatgacg gagaatacca aaagtcttat gataaatctc aagaggcttc tgactctata   180
gataaaacta ctgtatcatt attttataga ttaatgaact taagaatagc taaagcaaaa   240
aatgatgcaa ataagactat taatgaaata gaacaattag gtgcttctac tgataatgaa   300
tttaaaacaa aatatcaaga agctctaaaa ttctttgaag aaggaaataa tagtattact   360
aacttacctc cagaaccgca aactcctcct acagatgaag agtttactgc ttcttcaaac   420
acattcacta cagtatataa ttctttcaac aatgctttac aatctgctaa cagtgtaaaa   480
gaaggttatc ttaatagaga aagagcaata gcttcaaaat ccattaatga tgctagaaac   540
aaatataaag cagaattagg caagagtgta aaagcaggcg atgctaatga tagaaatatt   600
aatggtgctt taactagagc tgatgaagca cttagcaatg acaattttgc aagcgttcag   660
cagaatgtat ctactgcatt agctggtata aataaagcta tagcagatgc taaggcgaaa   720
gctgaggcag aagctaaagc aaaagctgct gctgaagcta aggcaagagc tgaagcagag   780
gctaaagcga aagcagaagc tgctgctaaa gcaaaagctg aagcagaggc taaagcgaaa   840
gcagatgcaa tagcaaaagc taaaaaagac atagaagatg cacaaaataa atataataat   900
ttagttaatg atcaagtaat agctaaaggt gatgataatg ataaaaacgt atcaaaactt   960
ttaactgatg ctaataatgc tttacaaaac actcctcaaa ctgcaagcga taaagcttta  1020
gaagcttcta aaactatgga taatatatta aacactgcta atcaattgaa aaaagaagaa  1080
gctgttaaaa atctagagca attaaaggca agaagagaca gacttataag cgaaggttat  1140
ttaactaaag acagcgaaga gaacaaaag ttatctcaaa ctattaaaga agctgaagat  1200
gctttaaata acaatgatta tgttttagct gaccaaaaaa tgcaggaagc taatcttaac  1260
atgaatgcta tagaagagag aggacctatt gacggacaag ttatacctgg tgaaatgggc  1320
ggtaacgaaa ctggtcaaat aattgatgct actactggtc aagaagtaaa tacagaagga  1380
aaagttactg tattacctca atattatgtt gtagtaagaa gagtacctct aactgatgct  1440
ttatggagaa ttgctggata cagctacata caacaacc ctatagaatg gtacagaata  1500
tatgaagcta acagaaatgt acttagagac cctaataacc ctgatttaat acttcctggt  1560
caaagattaa taatacctag ccttaatggt gaagagaga gcggtgatta taatcctgat  1620
ttagagtatt tgacttatga tgaggttatg cagttaagac agcaaaataa cactactcaa  1680
gcacaacagt aagaaataaa cttataaaat acaaaggtc atgcatttaa tatgtatgac  1740
ctttttttgt                                                         1750
```

<210> SEQ ID NO 2
<211> LENGTH: 564
<212> TYPE: PRT
<213> ORGANISM: Brachyspira pilosicoli

<400> SEQUENCE: 2

Met Ser Thr Leu Ile Lys Lys Ile Val Ala Tyr Ile Ala Leu Ile Ser
 1               5                  10                  15

Phe Ser Phe Ser Val Leu Pro Ala Gln Thr Tyr Asp Asp Ala Ala Arg
             20                  25                  30

Ile Thr Gly Glu Ala Glu Thr Leu Gln Asn Asp Gly Glu Tyr Gln Lys
         35                  40                  45

Ser Tyr Asp Lys Ser Gln Glu Ala Ser Asp Ser Ile Asp Lys Thr Thr
     50                  55                  60

-continued

```
Val Ser Leu Phe Tyr Arg Leu Met Asn Leu Arg Ile Ala Lys Ala Lys
 65                  70                  75                  80

Asn Asp Ala Asn Lys Thr Ile Asn Glu Ile Glu Gln Leu Gly Ala Ser
                 85                  90                  95

Thr Asp Asn Glu Phe Lys Thr Lys Tyr Gln Glu Ala Leu Lys Phe Phe
            100                 105                 110

Glu Glu Gly Asn Asn Ser Ile Thr Asn Leu Pro Pro Glu Pro Gln Thr
        115                 120                 125

Pro Pro Thr Asp Glu Glu Phe Thr Ala Ser Ser Asn Thr Phe Thr Thr
    130                 135                 140

Val Tyr Asn Ser Phe Asn Asn Ala Leu Gln Ser Ala Asn Ser Val Lys
145                 150                 155                 160

Glu Gly Tyr Leu Asn Arg Glu Arg Ala Ile Ala Ser Lys Ser Ile Asn
                165                 170                 175

Asp Ala Arg Asn Lys Tyr Lys Ala Glu Leu Gly Lys Ser Val Lys Ala
            180                 185                 190

Gly Asp Ala Asn Asp Arg Asn Ile Asn Gly Ala Leu Thr Arg Ala Asp
        195                 200                 205

Glu Ala Leu Ser Asn Asp Asn Phe Ala Ser Val Gln Gln Asn Val Ser
    210                 215                 220

Thr Ala Leu Ala Gly Ile Asn Lys Ala Ile Ala Asp Ala Lys Ala Lys
225                 230                 235                 240

Ala Glu Ala Glu Ala Lys Ala Lys Ala Ala Glu Ala Lys Ala Arg
                245                 250                 255

Ala Glu Ala Glu Ala Lys Ala Lys Ala Glu Ala Ala Lys Ala Lys
            260                 265                 270

Ala Glu Ala Glu Ala Lys Ala Lys Asp Ala Ile Ala Lys Ala Lys
        275                 280                 285

Lys Asp Ile Glu Asp Ala Gln Asn Lys Tyr Asn Asn Leu Val Asn Asp
    290                 295                 300

Gln Val Ile Ala Lys Gly Asp Asp Asn Asp Lys Asn Val Ser Lys Leu
305                 310                 315                 320

Leu Thr Asp Ala Asn Asn Ala Leu Gln Asn Thr Pro Gln Thr Ala Ser
                325                 330                 335

Asp Lys Ala Leu Glu Ala Ser Lys Thr Met Asp Asn Ile Leu Asn Thr
            340                 345                 350

Ala Asn Gln Leu Lys Lys Glu Glu Ala Val Lys Asn Leu Glu Gln Leu
        355                 360                 365

Lys Ala Arg Arg Asp Arg Leu Ile Ser Glu Gly Tyr Leu Thr Lys Asp
    370                 375                 380

Ser Glu Glu Glu Gln Lys Leu Ser Gln Thr Ile Lys Glu Ala Glu Asp
385                 390                 395                 400

Ala Leu Asn Asn Asn Asp Tyr Val Leu Ala Asp Gln Lys Met Gln Glu
                405                 410                 415

Ala Asn Leu Asn Met Asn Ala Ile Glu Glu Arg Gly Pro Ile Asp Gly
            420                 425                 430

Gln Val Ile Pro Gly Glu Met Gly Gly Asn Glu Thr Gly Gln Ile Ile
        435                 440                 445

Asp Ala Thr Thr Gly Gln Glu Val Asn Thr Glu Gly Lys Val Thr Val
    450                 455                 460

Leu Pro Gln Tyr Tyr Val Val Arg Arg Val Pro Leu Thr Asp Ala
465                 470                 475                 480
```

-continued

```
Leu Trp Arg Ile Ala Gly Tyr Ser Tyr Ile Tyr Asn Pro Ile Glu
            485                 490                 495

Trp Tyr Arg Ile Tyr Glu Ala Asn Arg Asn Val Leu Arg Asp Pro Asn
        500                 505                 510

Asn Pro Asp Leu Ile Leu Pro Gly Gln Arg Leu Ile Ile Pro Ser Leu
            515                 520                 525

Asn Gly Glu Glu Arg Ser Gly Asp Tyr Asn Pro Asp Leu Glu Tyr Leu
        530                 535                 540

Thr Tyr Asp Glu Val Met Gln Leu Arg Gln Gln Asn Asn Thr Thr Gln
545                 550                 555                 560

Ala Gln Gln Glx

<210> SEQ ID NO 3
<211> LENGTH: 32
<212> TYPE: PRT
<213> ORGANISM: Brachyspira pilosicoli
<220> FEATURE:
<223> OTHER INFORMATION: mp-72 protein fragment

<400> SEQUENCE: 3

Lys Val Thr Val Leu Pro Gln Tyr Tyr Val Val Arg Arg Val Pro
1               5                   10                  15

Leu Thr Asp Ala Leu Trp Arg Ile Ala Gly Tyr Ser Tyr Ile Tyr Asn
            20                  25                  30

<210> SEQ ID NO 4
<211> LENGTH: 22
<212> TYPE: PRT
<213> ORGANISM: Brachyspira pilosicoli
<220> FEATURE:
<223> OTHER INFORMATION: mp-72 protein fragment

<400> SEQUENCE: 4

Leu Ile Lys Lys Ile Val Ala Tyr Ile Ala Leu Ile Ser Phe Ser Phe
1               5                   10                  15

Ser Val Leu Pro Ala Gln
            20

<210> SEQ ID NO 5
<211> LENGTH: 13
<212> TYPE: PRT
<213> ORGANISM: Brachyspira pilosicoli
<220> FEATURE:
<223> OTHER INFORMATION: mp-72 protein fragment

<400> SEQUENCE: 5

Lys Thr Thr Val Ser Leu Phe Tyr Arg Leu Met Asn Leu
1               5                   10

<210> SEQ ID NO 6
<211> LENGTH: 7
<212> TYPE: PRT
<213> ORGANISM: Brachyspira pilosicoli
<220> FEATURE:
<223> OTHER INFORMATION: mp-72 protein fragment

<400> SEQUENCE: 6

Asn Asp Gln Val Ile Ala Lys
1               5

<210> SEQ ID NO 7
<211> LENGTH: 14
<212> TYPE: PRT
```

```
<213> ORGANISM: Brachyspira pilosicoli
<220> FEATURE:
<223> OTHER INFORMATION: mp-72 protein fragment

<400> SEQUENCE: 7

Asp Leu Ile Leu Pro Gly Gln Arg Leu Ile Ile Pro Ser Leu
 1               5                  10

<210> SEQ ID NO 8
<211> LENGTH: 8
<212> TYPE: PRT
<213> ORGANISM: Brachyspira pilosicoli
<220> FEATURE:
<223> OTHER INFORMATION: mp-72 protein fragment

<400> SEQUENCE: 8

Asn Asp Tyr Val Ala Leu Asp Gln
 1               5

<210> SEQ ID NO 9
<211> LENGTH: 18
<212> TYPE: PRT
<213> ORGANISM: Brachyspira pilosicoli
<220> FEATURE:
<223> OTHER INFORMATION: mp-72 protein fragment

<400> SEQUENCE: 9

Phe Ala Ser Val Gln Gln Asn Val Ser Thr Ala Leu Ala Gly Ile Asn
 1               5                  10                  15

Lys Ala

<210> SEQ ID NO 10
<211> LENGTH: 6
<212> TYPE: PRT
<213> ORGANISM: Brachyspira pilosicoli
<220> FEATURE:
<223> OTHER INFORMATION: mp-72 protein fragment

<400> SEQUENCE: 10

Val Ser Lys Leu Leu Thr
 1               5

<210> SEQ ID NO 11
<211> LENGTH: 13
<212> TYPE: PRT
<213> ORGANISM: Brachyspira pilosicoli
<220> FEATURE:
<223> OTHER INFORMATION: mp-72 protein fragment

<400> SEQUENCE: 11

Asp Leu Glu Tyr Leu Thr Tyr Asp Glu Val Met Gln Leu
 1               5                  10

<210> SEQ ID NO 12
<211> LENGTH: 8
<212> TYPE: PRT
<213> ORGANISM: Brachyspira pilosicoli
<220> FEATURE:
<223> OTHER INFORMATION: mp-72 protein fragment

<400> SEQUENCE: 12

Asn Ala Leu Gln Ser Ala Asn Ser
 1               5

<210> SEQ ID NO 13
<211> LENGTH: 7
```

```
<212> TYPE: PRT
<213> ORGANISM: Brachyspira pilosicoli
<220> FEATURE:
<223> OTHER INFORMATION: mp-72 protein fragment

<400> SEQUENCE: 13

Asp Gly Gln Val Ile Pro Gly
1               5

<210> SEQ ID NO 14
<211> LENGTH: 7
<212> TYPE: PRT
<213> ORGANISM: Brachyspira pilosicoli
<220> FEATURE:
<223> OTHER INFORMATION: mp-72 protein fragment

<400> SEQUENCE: 14

Val Lys Asn Leu Glu Gln Leu
1               5

<210> SEQ ID NO 15
<211> LENGTH: 7
<212> TYPE: PRT
<213> ORGANISM: Brachyspira pilosicoli
<220> FEATURE:
<223> OTHER INFORMATION: mp-72 protein fragment

<400> SEQUENCE: 15

Gly Lys Ser Val Lys Ala Gly
1               5

<210> SEQ ID NO 16
<211> LENGTH: 6
<212> TYPE: PRT
<213> ORGANISM: Brachyspira pilosicoli
<220> FEATURE:
<223> OTHER INFORMATION: mp-72 protein fragment

<400> SEQUENCE: 16

Gln Glu Ala Leu Lys Phe
1               5

<210> SEQ ID NO 17
<211> LENGTH: 7
<212> TYPE: PRT
<213> ORGANISM: Brachyspira pilosicoli
<220> FEATURE:
<223> OTHER INFORMATION: mp-72 protein fragment

<400> SEQUENCE: 17

Phe Thr Thr Val Tyr Asn Ser
1               5

<210> SEQ ID NO 18
<211> LENGTH: 7
<212> TYPE: PRT
<213> ORGANISM: Brachyspira pilosicoli
<220> FEATURE:
<223> OTHER INFORMATION: mp-72 protein fragment

<400> SEQUENCE: 18

Asn Leu Pro Pro Glu Pro Gln
1               5

<210> SEQ ID NO 19
<211> LENGTH: 7
<212> TYPE: PRT
```

-continued

```
<213> ORGANISM: Brachyspira pilosicoli
<220> FEATURE:
<223> OTHER INFORMATION: mp-72 protein fragment

<400> SEQUENCE: 19

Lys Ala Asp Ala Ile Ala Lys
 1               5

<210> SEQ ID NO 20
<211> LENGTH: 9
<212> TYPE: PRT
<213> ORGANISM: Brachyspira pilosicoli
<220> FEATURE:
<223> OTHER INFORMATION: mp72 protein fragment

<400> SEQUENCE: 20

Lys Ala Glu Ala Ala Ala Lys Ala Lys
 1               5

<210> SEQ ID NO 21
<211> LENGTH: 7
<212> TYPE: PRT
<213> ORGANISM: Brachyspira pilosicoli
<220> FEATURE:
<223> OTHER INFORMATION: mp-72 protein fragment

<400> SEQUENCE: 21

Lys Ala Lys Ala Ala Ala Glu
 1               5

<210> SEQ ID NO 22
<211> LENGTH: 6
<212> TYPE: PRT
<213> ORGANISM: Brachyspira pilosicoli
<220> FEATURE:
<223> OTHER INFORMATION: mp-72 protein fragment

<400> SEQUENCE: 22

Asp Lys Ala Leu Glu Ala
 1               5

<210> SEQ ID NO 23
<211> LENGTH: 20
<212> TYPE: DNA
<213> ORGANISM: T3 phage

<400> SEQUENCE: 23
taaccctcac taaagggaac                                          20

<210> SEQ ID NO 24
<211> LENGTH: 24
<212> TYPE: DNA
<213> ORGANISM: Artificial Sequence
<220> FEATURE:
<223> OTHER INFORMATION: AHP-F1 primer

<400> SEQUENCE: 24
tgaatgctat agaagagaga ggac                                     24

<210> SEQ ID NO 25
<211> LENGTH: 22
<212> TYPE: DNA
<213> ORGANISM: T7 phage

<400> SEQUENCE: 25
gtaatacgac tcactatagg gc                                       22
```

<210> SEQ ID NO 26
<211> LENGTH: 23
<212> TYPE: DNA
<213> ORGANISM: Artificial Sequence
<220> FEATURE:
<223> OTHER INFORMATION: pTrcHis-F primer

<400> SEQUENCE: 26
caatttatca gacaatctgt gtg                                          23

<210> SEQ ID NO 27
<211> LENGTH: 21
<212> TYPE: DNA
<213> ORGANISM: Artificial Sequence
<220> FEATURE:
<223> OTHER INFORMATION: AHP-Rev primer

<400> SEQUENCE: 27
tcgcttgcag tttgaggagt g                                            21

<210> SEQ ID NO 28
<211> LENGTH: 21
<212> TYPE: DNA
<213> ORGANISM: Artificial Sequence
<220> FEATURE:
<223> OTHER INFORMATION: AHP-Rev2 primer

<400> SEQUENCE: 28
tggattttga agctattgct c                                            21

<210> SEQ ID NO 29
<211> LENGTH: 22
<212> TYPE: DNA
<213> ORGANISM: Artificial Sequence
<220> FEATURE:
<223> OTHER INFORMATION: AHP-F4 primer

<400> SEQUENCE: 29
caagtaatag ctaaaggtga tg                                           22

<210> SEQ ID NO 30
<211> LENGTH: 22
<212> TYPE: DNA
<213> ORGANISM: Artificial Sequence
<220> FEATURE:
<223> OTHER INFORMATION: AHP-R783 primer

<400> SEQUENCE: 30
ttactgttgt gcttgagtag tg                                           22

<210> SEQ ID NO 31
<211> LENGTH: 24
<212> TYPE: DNA
<213> ORGANISM: Artificial Sequence
<220> FEATURE:
<223> OTHER INFORMATION: AHP-98F primer

<400> SEQUENCE: 31
cgtttagctg aacttgaagc tatg                                         24

<210> SEQ ID NO 32
<211> LENGTH: 21
<212> TYPE: DNA
<213> ORGANISM: Artificial Sequence
<220> FEATURE:

-continued

<223> OTHER INFORMATION: AHP+1890R primer

<400> SEQUENCE: 32
gtaatgctct gtcttaatca t                                              21

<210> SEQ ID NO 33
<211> LENGTH: 21
<212> TYPE: DNA
<213> ORGANISM: Artificial Sequence
<220> FEATURE:
<223> OTHER INFORMATION: AHP+1012R primer

<400> SEQUENCE: 33
tatcgcttgc agtttgagga g                                              21

<210> SEQ ID NO 34
<211> LENGTH: 34
<212> TYPE: DNA
<213> ORGANISM: Artificial Sequence
<220> FEATURE:
<223> OTHER INFORMATION: AHP-F1-Xho1 primer

<400> SEQUENCE: 34
agactcgaga gtactttaat aaagaaaatc gtag                                34

<210> SEQ ID NO 35
<211> LENGTH: 31
<212> TYPE: DNA
<213> ORGANISM: Artificial Sequence
<220> FEATURE:
<223> OTHER INFORMATION: AHP-R783-EcoR1 primer

<400> SEQUENCE: 35
gttgaattct tactgttgtg cttgagtagt g                                   31

<210> SEQ ID NO 36
<211> LENGTH: 31
<212> TYPE: DNA
<213> ORGANISM: Artificial Sequence
<220> FEATURE:
<223> OTHER INFORMATION: AHP-R223-EcoR1 primer

<400> SEQUENCE: 36
taagaattcc ttataagtct gtctcttctt g                                   31

<210> SEQ ID NO 37
<211> LENGTH: 31
<212> TYPE: DNA
<213> ORGANISM: Artificial Sequence
<220> FEATURE:
<223> OTHER INFORMATION: AHP-F4-Xho1 primer

<400> SEQUENCE: 37
ctactcgagc aagtaatagc taaaggtgat g                                   31

<210> SEQ ID NO 38
<211> LENGTH: 23
<212> TYPE: DNA
<213> ORGANISM: Artificial Sequence
<220> FEATURE:
<223> OTHER INFORMATION: pTrcHis-R primer

<400> SEQUENCE: 38
tgcctggcag ttccctactc tcg                                            23

BRACHYSPIRA PILOSICOLI 72 KDA OUTER-MEMBRANE PROTEIN AND DIAGNOSTIC AND THERAPEUTIC USES THEREOF

CROSS-REFERENCE TO RELATED APPLICATIONS

This application is a National Stage Application under § 371 of International Application Number PCT/AU2004/001783, filed Dec. 17, 2004, which claims priority from Australian Application No. 2003907017, filed Dec. 19, 2003.

FIELD OF THE INVENTION

The present invention relates generally to the field of intestinal spirochaetosis. Specifically, the invention relates to a novel *Brachyspira pilosicoli* amino acid sequence of a 72 kDa outer-membrane protein designated Bpmp-72 and the polynucleotide sequence that encodes it. More specifically, the invention relates to the use of these sequences in prophylactic ("vaccination") and therapeutic treatment of infections with *Brachyspira pilosicoli* ("intestinal spirochaetosis") in animal species, including birds, and human beings. The invention also relates to the serologic and molecular biology-based diagnosis of animals and human beings colonised by *B. pilosicoli*. The invention further relates to the screening of drugs for *B. pilosicoli* therapy. Finally, the invention relates to prophylactic, therapeutic and diagnostic compositions derived from the nucleotide and amino acid sequences described in this application.

BACKGROUND ART

Intestinal spirochaetosis (IS), also known as colonic spirochaetosis or spirochaetal diarrhoea, is an important production-limiting disease of pigs and adult layer and broiler breeder hens. IS results from infection of the large intestine with the intestinal spirochaete *Brachyspira* (formerly *Serpulina*) *pilosicoli*. This spirochaete also infects a number of other animal species, including dogs, as well as human beings. The associated disease is best understood and has been most studied in pigs.

The prevalence of the infection in the Australian pig industry is uncertain, but studies in Europe and Scandinavia suggest that 30% or more of pig herds are infected. The associated disease is a colitis/typhlitis with intermittent diarrhoea and reduced growth rates. The economic significance of the disease in pigs is not clear, but it may be large since, although it is milder than swine dysentery, it is generally much more prevalent.

*B. pilosicoli* also commonly infects adult chickens. In a recent survey in Australia, intestinal spirochaetes were recovered from 43% of broiler breeder flocks and 68% of layer flocks, and *B. pilosicoli* was the spirochaete involved in 44% of a subset of these flocks. Infected flocks had an average 14% wetter faeces than uninfected flocks. Experimental infection of broiler breeder hens with a *B. pilosicoli* isolate from this study resulted in a significant delay in onset of egg production and a sustained reduction in egg production. Besides layers, loss of egg production in broiler breeder flocks can cause considerable disruption to the whole broiler industry. The costs of these problems are difficult to estimate, but the Industries are significant in Australia. The Chicken Meat Industry produces meat with a retail value of $2.5 billion, whilst the Egg Industry produces eggs valued at $340 million.

The role of *B. pilosicoli* as a pathogen of dogs and other animal species is still not firmly established, although it seems likely that it is capable of impacting on health to a greater or lesser extent depending on a number of other factors. *B. pilosicoli* also infects large numbers of people in developing countries. In developed countries infection is mainly confined to immunocompromised individuals and homosexual males. It has been recorded as a cause of spirochaetaemia in elderly and/or immunocompromised individuals. The full extent of the pathogenic impact of *B. pilosicoli* in these human population groups is still debated.

Few attempts have been made to develop means to control infections with *B. pilosicoli*. When IS is identified as a problem in piggeries, animals are routinely treated with antimicrobials, although the disease tends to recur following withdrawal of treatment. However, the disease in chickens is not well understood, and the chicken industries have not specifically tried to control the infection.

There is only one recorded study of the use of a vaccine to control IS in pigs and this autogenous bacterin failed to offer protection (Hampson D J, Robertson I D, La T, Oxberry S L and Pethick D W (2000) Influences of diet and vaccination on colonization of pigs by the intestinal spirochaete *Brachyspira* (*Serpulina*) *pilosicoli*. Veterinary Microbiology 74:75-84). Nevertheless, because there is a specific end-on attachment of the spirochaete to the large intestinal mucosa, it seems likely that colonisation can be reduced or prevented by the use of a suitable vaccine-induced immunity.

The present invention provides a novel *B. pilosicoli* amino acid sequence and the polynucleotide sequence that encodes it, which has not previously been identified.

SUMMARY OF THE INVENTION

We have identified a novel amino acid sequence, referred to herein as *B. pilosicoli* membrane protein 72 (Bpmp-72), as well as amino acid fragments thereof that are particularly suited to diagnostic, prophylactic and therapeutic purposes associated with intestinal spirochaetosis. We have also identified the polynucleotide sequence encoding the Bpmp-72 amino acid sequence.

Accordingly, the present invention provides a Bpmp-72 amino acid sequence which comprises the sequence set out in SEQ ID NO:2 or an amino acid sequence substantially homologous thereto, or a fragment of the amino acid sequence of SEQ ID NO:2. In one preferred embodiment of the invention there are provided fragments of the Bpmp-72 amino acid sequence, which are selected from SEQ ID NO:3 to SEQ ID NO:22.

The invention also provides a Bpmp-72 polynucleotide sequence (SEQ ID NO:1) or a homologue thereof. Preferably, the Bpmp-72 polynucleotide sequence is selected from: (a) polynucleotide sequences comprising the nucleotide sequence set out in SEQ ID NO:1 or a fragment thereof; (b) polynucleotide sequences comprising a nucleotide sequence capable of selectively hybridising to the polynucleotide sequence set out in SEQ ID NO:1 or a fragment thereof; (c) polynucleotide sequences that are degenerate, as a result of the genetic code, to the sequences defined in (a) or (b), or (d) Polynucleotide sequences complementary to the sequences of (a), (b) or (c).

Detectably labelled nucleotide sequences hybridisable to a polynucleotide sequence of the invention are also provided and include nucleotide sequences hybridisable to a coding or non-coding region of a Bpmp-72 polynucleotide sequence. The present invention also provides oligonucleotide primers for amplifying *B. pilosicoli* genomic DNA encoding a Bpmp- 72 amino acid sequence such as set out in SEQ ID NO:24, and SEQ ID NOS:27 through to SEQ ID NO:37.

Vectors provided by the invention will contain a Bpmp-72 polynucleotide sequence according to the invention. Preferably, the vectors are either cloning or expression vectors. Where the vector is an expression vector, it preferentially comprises a Bpmp-72 polynucleotide sequence operatively associated with an expression control sequence.

Also provided are cells transformed or transfected with a polynucleotide sequence of the invention or with a vector as described above. Preferred cells include: bacteria, yeast, mammalian cells, plant cells, insect cells, or swine cells in tissue culture.

The invention further provides methods for preparing a Bpmp-72 amino acid sequence comprising: (a) culturing a cell as described above under conditions that provide for expression of a Bpmp-72 amino acid sequence; and (b) recovering the expressed Bpmp-72 amino acid sequence. This procedure can also be accompanied by the steps of: (c) chromatographing the amino acid sequence on a Ni-chelation column; and (d) purifying the amino acid sequence by gel filtration.

The invention also provides labelled and unlabeled monoclonal and polyclonal antibodies specific for a Bpmp-72 amino acid sequence of the invention and immortal cell lines that produce a monoclonal antibody of the invention. Antibody preparation according to the invention involves: (a) conjugating a Bpmp-72 amino acid sequence to a carrier protein; (b) immunising a host animal with the Bpmp-72 amino acid sequence fragment-carrier protein conjugate of step (a) admixed with an adjuvant; and (c) obtaining Bpmp-72 specific antibody from the immunised host animal.

The invention further provides a method for detecting the presence or absence of *Brachyspira* species, including but not limited to *B. hyodysenteriae, B. intermedia, B. alvinipulli, B. aalborgi* and *B. pilosicoli* in a biological sample, which method comprises: (a) bringing the biological sample into contact with a polynucleotide probe or primer comprising a Bpmp-72 polynucleotide sequence of the invention under suitable hybridising conditions; and (b) detecting any duplexes formed between the probe or primer and the nucleotide sequences in the sample.

The invention provides methods for measuring the presence of a Bpmp-72 amino acid sequence in a sample, comprising: (a) contacting a sample suspected of containing a Bpmp-72 amino acid sequence with an antibody that specifically binds to the Bpmp-72 amino acid sequence under conditions which allow for the formation of a reaction complex; and (b) detecting the formation of the reaction complex, wherein detection of the formation of a reaction complex indicates the presence of a Bpmp-72 amino acid sequence in the sample.

The invention also provides a method for detecting intestinal spirochaetosis antibodies in biological samples, which comprises: (a) providing a Bpmp-72 amino acid sequence or a fragment thereof; (b) incubating a biological sample with said amino acid sequence under conditions which allow for the formation of an antibody antigen complex; and (c) detecting said antibody-antigen complex.

Correspondingly provided are in vitro methods for evaluating the level of Bpmp-72 amino acid sequence in a biological sample comprising: (a) detecting the formation of reaction complexes in a biological sample according to the method noted above; and (b) evaluating the amount of reaction complexes formed, which amount corresponds to the level of Bpmp-72 amino acid sequence in the biological sample.

Further, there are provided in vitro methods for monitoring therapeutic treatment of a disease associated with *Brachyspira* species, including but not limited to *B. hyodysenteriae, B. intermedia, B. alvinipulli, B. aalborgi* and *B. pilosicoli* in an animal host comprising evaluating, as describe above, the levels of Bpmp-72 amino acid sequence in a series of biological samples obtained at different time points from an animal host undergoing such therapeutic treatment.

The invention also addresses the use of polynucleotide sequences of the invention, as well as antisense nucleic acid sequences hybridisable to a polynucleotide encoding an Bpmp-72 amino acid sequence according to the invention, for the manufacture of a medicament for modulation of a disease associated with *Brachyspira* species, including but not limited to *B. hyodysenteriae, B. intermedia, B. alvinipulli, B. aalborgi* and *B. pilosicoli*.

Additionally, the invention provides pharmaceutical or therapeutic compositions or agents, including but not limited to vaccines for the prevention, amelioration or treatment of intestinal spirochaetes associated with *Brachyspira* species, including but not limited to *B. hyodysenteriae, B. intermedia, B. alvinipulli, B. aalborgi* and *B. pilosicoli* comprising: (a) at least a Bpmp-72 amino acid sequence as described herein or at least a Bpmp-72 nucleotide sequence as described herein or an antibody that specifically bind to one of the aforementioned sequences; and (b) one or more pharmaceutically acceptable carriers and/or diluents.

The invention further provides a polynucleotide, amino acid sequence and/or antibody of the invention for use in therapy. Also provided is a method of treating a condition characterised by intestinal spirochaetosis, which method comprises administering to an animal in need of treatment an effective amount of a polynucleotide, amino acid sequence or antibody of the invention. Further, the invention provides a method for prophylactically treating an animal to prevent or at least minimise intestinal spirochaetosis, comprising the step of: administering to the animal an effective amount of a polynucleotide, polypeptide, an antibody or a pharmaceutical composition comprising one or more of these biological molecules.

In addition, the invention provides methods of screening drugs capable of modulating the biological activity of *Brachyspira* species, including but not limited to *B. hyodysenteriae, B. intermedia, B. alvinipulli, B. aalborgi* and *B. pilosicoli* through either direct or indirect interaction with a Bpmp-72 nucleotide or amino acid sequence. A substance identified by these methods may be used in a method of treating intestinal spirochaetosis.

The invention also provides kits for screening animals suspected of being infected with *Brachyspira* species, including but not limited to *B. hyodysenteriae, B. intermedia, B. alvinipulli, B. aalborgi* and *B. pilosicoli* or to confirm that an animal is infected with a *Brachyspira* species, such as *B. pilosicoli*, which kits comprise at least a polynucleotide complementary to a portion of the Bpmp-72 polynucleotide sequence, packaged in a suitable container, together with instructions for its use. In an alternate form, the invention provides kits for (a) screening host animals suspected of being infected with a *Brachyspira* species, such as *B. pilosicoli*, or (b) to confirm that a host animal is infected with a *Brachyspira* species, such as *B. pilosicoli*, which kits comprise at least a Bpmp-72 amino acid sequence or fragment thereof or an antibody which binds the aforementioned sequences packaged in a suitable container and instructions for its use.

Other aspects and advantages of the invention will become apparent to those skilled in the art from a review of the ensuing description, which proceeds with reference to the following illustrative drawings.

BRIEF DESCRIPTION OF THE DRAWINGS

FIG. 3 Nucleotide sequence of Bpmp-72 (SEQ ID NO:39.

DETAILED DISCLOSURE OF THE INVENTION

General

Figure 1:
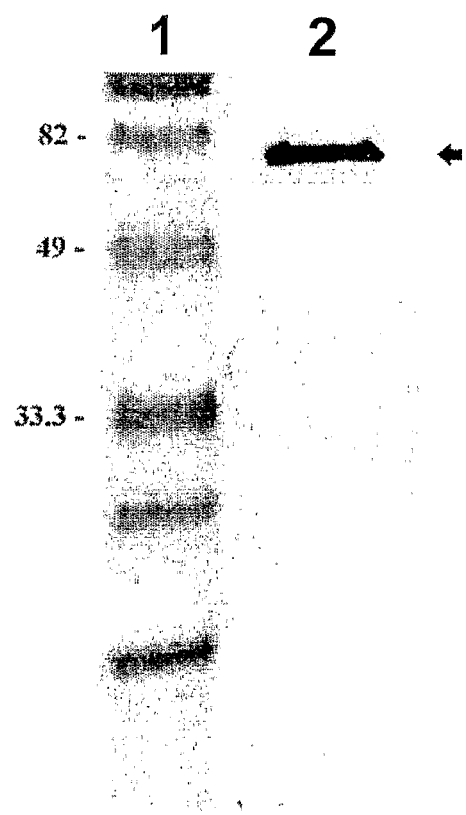
FIG. 1 Western Blot analysis of the absorbed hyper-immunised pig serum (AHPS) with *B. pilosicoli* outer membrane proteins. Lane 1, molecular weight markers; lane 2, *B. pilosicoli* 95/1000. The 72 kDa protein (Bpmp-72) is indicated with the arrow.

Those skilled in the art will appreciate that the invention described herein is susceptible to variations and modifications other than those specifically described. It is to be understood that the invention includes all such variation and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

Sequence identity numbers (SEQ ID NO:) containing nucleotide and amino acid sequence information included in this specification are collected at the end of the description and have been prepared using the programme PatentIn Version 3.2. Each nucleotide or amino acid sequence is identified in the sequence listing by the numeric indicator <210> followed by the sequence identifier (e.g. <210> 1, <210> 2, etc.). The length, type of sequence and source organism for each nucleotide or amino acid sequence are indicated by information provided in the numeric indicator fields <211>, <212> and <213>, respectively. Nucleotide and amino acid sequences referred to in the specification are defined by the information provided in numeric indicator field <400> followed by the sequence identifier (e.g. <400>1, <400>2, etc.).

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

As used herein the term "derived" and "derived from" shall be taken to indicate that a specific integer may be obtained from a particular source albeit not necessarily directly from that source.

Throughout this specification, unless the context requires otherwise, the word "comprise", or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

DETAILED DESCRIPTION OF THE INVENTION

The present invention relates to the identification of Bpmp-72 amino acid sequences, including variations and fragments thereof as well as polynucleotide sequences encoding said sequences.

The Bpmp-72 amino acid sequence was isolated from *B. pilosicoli* by screening a *B. pilosicoli* lambda bacteriophage genomic library. Through this screening process six clones, designated AHP1-6, were found. These clones all produced a common protein with an apparent molecular weight of 34 kDa, all of which reacted strongly with the absorbed hyper-immunised pig serum. Sequencing of one clone identified a 783 base pair partial open-reading frame (ORF) with a coding capacity of 29.4 kDa. This partial ORF may encode the carboxy-terminal portion of the 72 kDa outer-membrane protein of *B. pilosicoli*.

Homology searches of Bpmp-72 against the SWISS-PROT database identified approximately 5% homology between this protein and Treponemal membrane protein B (TmpB) of *Treponema phagedenis* and *Treponema pallidum* (Table 1). These proteins are outer-membrane associated and may serve as porins or transport proteins for large molecules. Comparison of the Bpmp-72 nucleotide sequence with the GenBank nucleotide database did not reveal any strong homology with other bacterial genes.

TABLE 1

| Organism | Protein | Size (aa) | Identity (aa) | Homology (%) | Accession Number |
|---|---|---|---|---|---|
| *Treponema pallidum* | TmpB | 325 | 33 | 5.85 | P19649 |
| *Treponema phagedenis* | TmpB | 384 | 32 | 5.67 | P29720 |

Analysis of the Bpmp-72 polynucleotide sequence revealed a 1009 base pair insert of *B. pilosicoli* genomic DNA (FIG. 3). Sequence analysis of the insert DNA revealed a potential partial ORF of 783 base pair from bases 1 to 783, with a putative ATG start codon and a TAA stop codon. Further cloning and sequencing of the remaining gene revealed the coding sequence of Bpmp-72 to be 1,689 nucleotides in size. A potential Shine-Dalgarno ribosome binding site (AGGAG), and putative −10 (TAATAT) and −35 (TTGAAA) promoter regions were identified upstream from the ATG start codon. The gene sequence encoding the 72 kDa outer-membrane protein was designated outer-membrane protein of 72 kDa molecular weight (Bpmp-72).

Figure 4:
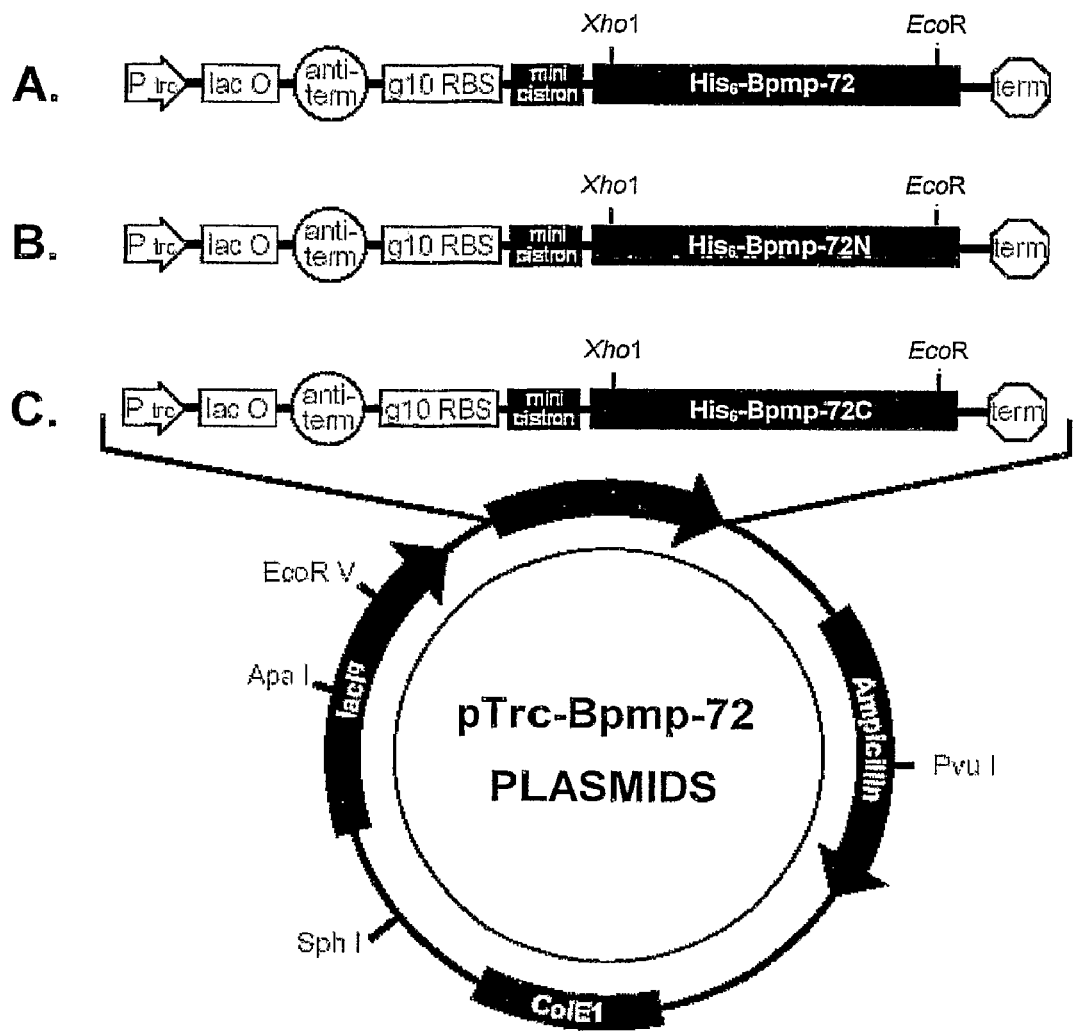
FIG. 4 Vector diagrams of the various regions of Bpmp-72 gene (designated Omp-72 in the figure) cloned into the pTrcHis *E. coli* expression vector. The pTrc-Bpmp-72 (A; 6,081 bp), pTrc-Bpmp-72N (B; 5,518 bp) and pTrc-Bpmp-72C(C; 5,171 bp) constructs express the full Bpmp-72, N-terminal portion of Bpmp-72 and C-terminal portion of Bpmp-72, respectively. All vectors were constructed from the same vector back-bone and differ only by the Bpmp-72 region cloned into the expression cassette.

The translated polypeptide consisted of 563 amino acid (aa) residues with a predicted molecular weight of 62.1 kDa (FIG. 4). The deduced size differed significantly from those seen in the Western blots of the native Bpmp-72 protein. The difference in molecular weight between the hypothetical coding capacity of Bpmp-72 and the native Bpmp-72 outer-membrane protein is probably due to post-translational modifications such as acylation, methylation, acetylation, phosphorylation and sulphation.

Analysis of the amino acid sequence revealed the presence of a 118 residue region at the C-terminus of the translated polypeptide which was homologous to a conserved lysine motif (LysM) domain. This domain is a widespread protein module which was originally identified in enzymes which degrade bacterial cell walls although it has since been shown to be present in many other bacterial proteins. The LysM domain is one of the most common modules in bacterial cell surface proteins. Other bacterial proteins which possess the LysM domain, such as Staphlococci IgG binding proteins and *E. coli* intimin, are involved in bacterial pathogenesis.

Bpmp-72 Amino Acid Sequences

Full-length Bpmp-72 amino acid sequences provided according to the invention will have about 563 amino acid (aa) residues and encode a *B. pilosicoli* outer membrane protein. The deduced molecular weight of the protein is 62,081 Da.

Bpmp-72 amino acid sequences of the invention include those having the amino acid sequence set forth herein e.g., SEQS ID NO: 2 through to 22. They also include Bpmp-72 amino acid sequences modified with conservative amino acid substitutions, as well as analogues, fragments and derivatives thereof.

In a preferred form of the invention there is provided an isolated Bpmp-72 amino acid sequence as herein described. More desirably the Bpmp-72 amino acid sequence is provided in substantially purified form.

The term "isolated" is used to describe a Bpmp-72 amino acid sequence that has been separated from components that accompany it in its natural state. Further, a Bpmp-72 amino acid sequence is "substantially purified" when at least about 60 to 75% of a sample exhibits a single Bpmp-72 amino acid sequence. A substantially purified Bpmp-72 amino acid sequence will typically comprise about 60 to 90% W/W of a Bpmp-72 amino acid sequence sample, more usually about 95%, and preferably will be over about 99% pure. Protein purity or homogeneity may be indicated by a number of means well known in the art, such as polyacrylamide gel electrophoresis of a protein sample, followed by visualizing a single Bpmp-72 amino acid sequence band upon staining the gel. For certain purposes, higher resolution may be provided by using HPLC or other means well known in the art which are utilised for application.

Preferred Bpmp-72 amino acid sequences of the invention will have one or more biological properties (eg in vivo, in vitro or immunological properties) of the native full-length Bpmp-72 amino acid sequence. Non-functional Bpmp-72 amino acid sequences are also included within the scope of the invention since they may be useful, for example, as antagonists of Bpmp-72. The biological properties of analogues, fragments, or derivatives relative to wild type may be determined, for example, by means of biological assays.

Bpmp-72 amino acid sequences, including analogues, fragments and derivatives, can be prepared synthetically (e.g., using the well known techniques of solid phase or solution phase peptide synthesis). Preferably, solid phase synthetic techniques are employed. Alternatively, Bpmp-72 amino acid sequences of the invention can be prepared using well known genetic engineering techniques, as described infra. In yet another embodiment, Bpmp-72 amino acid sequences can be purified (e.g., by immunoaffinity purification) from a biological fluid, such as but not limited to plasma, faeces, serum, or urine from animals, including pigs, chickens, human beings and dogs, horses, cattle, sheep and fish.

Analogues of the Bpmp-72 Amino Acid Sequence

Bpmp-72 amino acid sequence analogues include those having the amino acid sequence, wherein one or more of the amino acids is substituted with another amino acid which substitutions do not substantially alter the biological activity of the molecule.

In the context of the invention, an analogous sequence is taken to include a Bpmp-72 amino acid sequence which is at least 60, 70, 80 or 90% homologous, preferably at least 95 or 98% homologous at the amino acid level over at least 20, 50, 100 or 200 amino acids, with the amino acid sequences set out in SEQ ID NO:2. In particular, homology should typically be considered with respect to those regions of the sequence known to be essential for the function of the protein rather than non-essential neighbouring sequences. Particularly preferred amino acid sequences of the invention comprise a contiguous sequence having greater than 60 or 70% homology, more preferably greater than 80 to 90% homology, to one or more of amino acid sequences shown as SEQ ID NOs:3 to 22.

Although homology can be considered in terms of similarity (i.e. amino acid residues having similar chemical properties/functions), in the context of the present invention it is preferred to express homology in terms of sequence identity. The terms "substantial homology" or "substantial identity", when referring to Bpmp-72 amino acid sequences, indicate that the Bpmp-72 amino acid sequence in question exhibits at least about 70% identity with an entire naturally-occurring Bpmp-72 amino acid sequence or portion thereof, usually at least about 80% identity and preferably at least about 90 or 95% identity.

In a highly preferred form of the invention a Bpmp-72 amino acid sequence analogue will have 80% or greater amino acid sequence identity to the Bpmp-72 amino acid sequence set out in SEQ ID NO:2 or to a sequences as shown in SEQ ID NO: 3 through SEQ ID NO:22. Examples of Bpmp-72 amino acid sequence analogues within the scope of the invention include the amino acid sequence of SEQ ID NO:2 wherein: (a) one or more aspartic acid residues is substituted with glutamic acid; (b) one or more isoleucine residues is substituted with leucine; (c) one or more glycine or valine residues is substituted with alanine; (d) one or more arginine residues is substituted with histidine; or (e) one or more tyrosine or phenylalanine residues is substituted with tryptophan.

Screening for Bpmp-72 Analogues

Various screening techniques are known in the art for screening for analogues of polypeptides. Various libraries of chemicals are available. Accordingly, the present invention contemplates screening such libraries, e.g., libraries of synthetic compounds generated over years of research, libraries of natural compounds and combinatorial libraries, as described in greater detail, infra, for analogues of the Bpmp-72 amino acid sequence. In one embodiment, the invention contemplates screening such libraries for analogues that bind to Bpmp-72 specific antibodies.

Fragments of the Bpmp-72 Amino Acid Sequences

In addition to analogues, the invention contemplates fragments of the Bpmp-72 amino acid sequence. A Bpmp-72 amino acid sequence fragment is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids. Preferred Bpmp-72 amino acid sequence fragments include those sequences as shown in SEQ ID NO:3 through SEQ ID NO:22.

In a highly preferred form of the invention the fragments exhibit ligand-binding, immunological activity and/or other biological activities characteristic of Bpmp-72 amino acid sequences. More preferably, the fragments possess immunological epitopes consistent with those present on native Bpmp-72 amino acid sequences.

As used herein, "epitope" refers to an antigenic determinant of a polypeptide. An epitope could comprise three amino acids in a spatial conformation that is unique to the epitope. Generally, an epitope consists of at least five amino acids, and more usually consists of at least 8-10 amino acids. Methods of determining the spatial conformation of such amino acids are known in the art.

Bpmp-72 Amino Acid Sequence Derivatives

"Bpmp-72 amino acid sequence derivatives" are provided by the invention and include Bpmp-72 amino acid sequences, analogues or fragments thereof which are substantially homologous in primary structure but which include, chemical and/or biochemical modifications or unusual amino acids. Such modifications include, for example, acetylation, carboxylation, phosphorylation, glycosylation, ubiquitination, labelling, (e.g., with radionucleotides), and various enzymatic modifications, as will be readily appreciated by those well skilled in the art.

In one form of the invention the chemical moieties suitable for derivatisation are selected from among water soluble polymers. The polymer selected should be water soluble so that the protein to which it is attached does not precipitate in an aqueous environment, such as a physiological environment. Preferably, for therapeutic use of the end-product preparation, the polymer will be pharmaceutically acceptable. One skilled in the art will be able to select the desired polymer based on considerations such as whether the polymer/protein conjugate will be used therapeutically, and if so, the desired dosage, circulation time, resistance to proteolysis and other considerations. For the present proteins and peptides, these may be ascertained using the assays provided herein.

The water soluble polymer may be selected from the group consisting of, for example, polyethylene glycol, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, polypropylene oxide/ethylene oxide co-polymers, polyoxyethylated polyols and polyvinyl alcohol. Polyethylene glycol propionaldenhyde may provide advantages in manufacturing due to its stability in water.

In another form of the invention the amino acid sequences may be modified to produce a longer half life in an animal host, for example, by fusing one or more antibody fragments (such as an Fc fragment) to the amino or carboxyl end of a Bpmp-72 amino acid sequence.

Where the Bpmp-72 amino acid sequence is to be provided in a labelled form, a variety of methods for labelling amino acid sequences are well known in the art and include radioactive isotopes such as $^{32}P$, ligands which bind to labelled antiligands (eg, antibodies), fluorophores, chemiluminescent agents, enzymes and antiligands which can serve as specific binding pair members for a labelled ligand. The choice of label depends on the sensitivity required, stability requirements, and available instrumentation. Methods of labelling amino acid sequences are well known in the art [See, e.g., Sambrook et al., *Molecular Cloning: A Laboratory Manual*, Second Edition, Cold Spring Harbor Laboratory Press, Cold Spring Harbor, N.Y. (1989); and Ausubel, F., Brent, R., Kingston, R. E., Moore, D. D., Seidman, J. G., Smith, J. A., Struhl, K. *Current protocols in molecular biology*. Greene Publishing Associates/Wiley Intersciences, New York (2001)].

The Bpmp-72 amino acid sequences of the invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

The invention also provides for fusion polypeptides, comprising Bpmp-72 amino acid sequences and fragments. Thus Bpmp-72 amino acid sequences may be fusions between two or more Bpmp-72 amino acid sequences or between a Bpmp-72 amino acid sequence and a related protein. Likewise, heterologous fusions may be constructed which would exhibit a combination of properties or activities of the derivative proteins. For example, ligand-binding or other domains may be "swapped" between different fusion polypeptides or fragments. Such homologous or heterologous fusion polypeptides may display, for example, altered strength or specificity of binding. Fusion partners include immunoglobulins, bacterial beta-galactosidase, trpE, protein A, beta-lactamase, alpha amylase, alcohol dehydrogenase and yeast alpha mating factor.

Modified Bpmp-72 amino acid sequences may be synthesised using conventional techniques, or may be encoded by a modified polynucleotide sequence and produced using recombinant nucleic acid methods. The modified polynucleotide sequence may also be prepared by conventional techniques. Fusion proteins will typically be made by either recombinant nucleic acid methods or may be chemically synthesised.

Bpmp-72 Polynucleotides

According to the invention there is provided an isolated or substantially pure Bpmp-72 polynucleotide sequence, which encodes a Bpmp-72 amino acid sequence, or analogue, fragment, or derivative thereof. Preferred Bpmp-72 polynucleotide sequences according to the invention comprise the sequence set out in SEQ ID NO:1 or fragments thereof.

A "Bpmp-72 polynucleotide sequence" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single-stranded form, or a double-stranded helix. Double-stranded DNA-DNA, DNA-RNA and RNA-RNA helices are possible. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

An "isolated" or "substantially pure" Bpmp-72 polynucleotide is one that is substantially separated from other cellular components that naturally accompany a native *B. pilosicoli* genomic sequence. The term embraces a Bpmp-72 polynucleotide sequence that has been removed from its naturally occurring environment and includes recombinant or cloned Bpmp-72 polynucleotide sequence isolates and chemically synthesised variants or variants biologically synthesised by heterologous systems.

In one embodiment, the invention provides Bpmp-72 polynucleotide sequences for expression of a Bpmp-72 amino acid sequence. More specifically, the Bpmp-72 polynucleotide sequence is selected from the group consisting of: (a) polynucleotide sequences set out in SEQ ID NO:1 or fragments thereof; (b) polynucleotide sequences that hybridise to the polynucleotide sequence defined in (a) or hybridisable fragments thereof; and (c) polynucleotide sequences that code on expression for the amino acid sequence encoded by any of the foregoing polynucleotide sequences.

Homologous Bpmp-72 Polynucleotide Sequences

Bpmp-72 polynucleotide sequences of the invention will include a sequence that is either derived from, or substantially similar to a natural Bpmp-72 polynucleotide sequence or one having substantial homology with a natural Bpmp-72 polynucleotide sequence or a portion thereof. A Bpmp-72 polynucleotide sequence is "substantially homologous" ("or substantially similar") to another if, when optimally aligned (with appropriate nucleotide insertions or deletions) with the other polynucleotide sequence (or its complementary strand), there is nucleotide sequence identity in at least about 60% of the nucleotide bases, usually at least about 70%, more usually at least about 80%, preferably at least about 90% and more preferably at least about 95-98% of the nucleotide bases.

Alternatively, substantial homology or identity exists when a Bpmp-72 polynucleotide sequence or fragment thereof will hybridise to another Bpmp-72 polynucleotide (or a complementary strand thereof) under selective hybridisation conditions, to a strand, or to its complement. Selective hybridisation may be under low, moderate or high stringency conditions but is preferably under high stringency. Typically, selective hybridisation will occur when there is at least about 55% identity over a stretch of at least about 14 nucleotides, preferably at least about 65%, more preferably at least about 75% and most preferably at least about 90%. The length of homology comparison, as described, may be over longer stretches and in certain embodiments will often be over a stretch of at least about nine nucleotides, usually at least about 20 nucleotides, more usually at least about 24 nucleotides, typically at least about 28 nucleotides, more typically at least about 32 nucleotides and preferably at least about 36 or more nucleotides.

Thus, the polynucleotide sequences of the invention preferably have at least 75%, more preferably at least 85%, more preferably at least 90% homology to the sequences shown in the sequence listings herein. More preferably there is at least 95%, more preferably at least 98%, homology. Nucleotide homology comparisons may be conducted as described below for polypeptides. A preferred sequence comparison program is the GCG Wisconsin Bestfit program.

In the context of the present invention, a homologous sequence is taken to include a nucleotide sequence which is at least 60, 70, 80 or 90% identical, preferably at least 95 or 98% identical at the nucleic acid level over at least 20, 50, 100, 200, 300, 500 or 819 nucleotides with the nucleotides sequences set out in SEQ ID NO:1. In particular, homology should typically be considered with respect to those regions of the sequence that encode contiguous amino acid sequences known to be essential for the function of the protein rather than non-essential neighbouring sequences.

Other preferred Bpmp-72 polynucleotide sequences of the invention comprise a contiguous sequence having greater than 50, 60 or 70% homology, more preferably greater than 80, 90, 95 or 97% homology, to the nucleotide sequence that encodes one or more of the amino acid sequences of SEQ ID NO:3 to SEQ ID NO:22.

Bpmp-72 Polynucleotide Sequence Fragments

Bpmp-72 polynucleotide sequence fragments of the invention will preferably be at least 15 nucleotides in length, more preferably at least 20, 30, 40, 50, 100 or 200 nucleotides in length. Generally, the shorter the length of the polynucleotide sequence, the greater the homology required to obtain selective hybridisation. Consequently, where a polynucleotide sequence of the invention consists of less than about 30 nucleotides, it is preferred that the percentage identity is greater than 75%, preferably greater than 90% or 95% compared with the polynucleotide sequences set out in the sequence listings herein. Conversely, where a polynucleotide sequence of the invention consists of, for example, greater than 50 or 100 nucleotides, the percentage identity compared with the polynucleotide sequences set out in the sequence listings herein may be lower, for example greater than 50%, preferably greater than 60 or 75%.

Bpmp-72 Probe Sequences

Contemplated within the scope of the present invention are probe sequences derived from Bpmp-72 polynucleotide sequences, which can be conveniently prepared from the specific sequences disclosed herein. Probes may be of any suitable length, which span all or a portion of the Bpmp-72 polynucleotide sequence and which allow specific hybridisation to that sequence.

The greater the degree of homology, the more stringent the hybridisation conditions that can be used. Thus, in one embodiment, preferably the probes are designed so that low stringency hybridisation conditions are used to identify homologous Bpmp-72 polynucleotide sequences. In an alternate embodiment the probes are designed such that moderate hybridisation conditions are used. More preferably highly stringent conditions are used. As demonstrated experimentally herein, a Bpmp-72 probe sequence will hybridise to a polynucleotide sequence such as depicted in SEQ ID NO:1 under moderately stringent conditions; more preferably, it will hybridise under high stringency conditions.

Those skilled in the art will recognise that the stringency of hybridisation will be affected by such conditions as salt concentration, temperature, or organic solvents, in addition to the base composition, length of the complementary strands and the number of nucleotide base mismatches between the hybridising nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. An example of stringent hybridisation conditions is 65° C. and 0.1× SSC (1× SSC=0.15 M NaCl, 0.015 M sodium citrate pH 7.0).

Preferably, the probe sequences will have a nucleotide sequence of at least about eight consecutive nucleotides from SEQ ID NO:1, or preferably about 15 consecutive nucleotides, or more preferably at least about 25 nucleotides, and may have a minimal size of at least about 40 nucleotides. Particularly preferred, oligonucleotide probes for detecting Bpmp-72 polynucleotide sequences include the oligonucleotide sequences set out in SEQ ID NO:3 to SEQ ID NO:18 and in the Examples.

The probes of the invention may include an isolated polynucleotide attached to a label or reporter molecule and may be used to isolate other polynucleotide sequences, having sequence similarity by standard methods. For techniques for preparing and labelling probes see, e.g. Sambrook et al., (1989) supra or Ausubel et al., (2001) supra.

Probes comprising synthetic oligonucleotides or other polynucleotide sequences of the present invention may also be derived from naturally occurring or recombinant single- or double-stranded polynucleotides, or be chemically synthesised. Probes may be labelled by nick translation, Klenow fill-in reaction, or other methods known in the art.

Bpmp-72 Primer Sequences

The present invention also provides Bpmp-72 primer sequences. Primers employed in amplification reactions are preferably single stranded for maximum efficiency in amplification, but may be double stranded. If double stranded, primers may be first treated to separate the strands before being used to prepare extension products. Primers should be sufficiently long to prime the synthesis of Bpmp-72 extension products in the presence of the inducing agent for polymerisation. The exact length of a primer will depend on many factors, including temperature, buffer, and nucleotide composition.

Oligonucleotide primers will typically contain 12-20 or more nucleotides, although they may contain fewer nucleotides. Preferably, the primers are selected from the sequences depicted in SEQ ID NO: 3 to SEQ ID NO: 18.

Oligonucleotide primers may be prepared using any suitable method, such as conventional phosphotriester and phosphodiester methods or automated embodiments thereof. In one such automated embodiment, diethylphosphoramidites are used as starting materials and may be synthesized as described by Beaucage, et al., (1981) *Tetrahedron Letters*, 22:1859-1862. One method for synthesising oligonucleotides on a modified solid support is described in U.S. Pat. No. 4,458,066.

Antisense Nucleic Acids and Ribozymes

The present invention also extends to the preparation of antisense nucleotides and ribozymes that may be used to interfere with the expression of Bpmp-72 amino acid sequences at the translational level. This approach utilises antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule [See: Weintraub, (1990) *Sci. Am.*, 262:40-46; Marcus-Sekura, (1988) *Anal. Biochem.*, 172:289-295]. In the cell, they hybridise to that mRNA, forming a double-stranded molecule. The cell does not translate an mRNA complexed in this double-stranded form. Therefore, antisense nucleic acids interfere with the expression of mRNA into protein. Oligomers of about fifteen nucleotides and molecules that hybridise to the AUG initiation codon will be particularly efficient, since they are easy to synthesize and are likely to pose fewer problems than larger molecules when introducing them into infected cells. Antisense methods have been used to inhibit the expression of many genes in vitro [Hambor et al., (1988) *J. Exp. Med.,* 168:1237-1245].

Ribozymes are RNA molecules possessing the ability to specifically cleave other single-stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognise specific nucleotide sequences in an RNA molecule and cleave it [Cech, (1988) *J. Am. Med. Assoc.,* 260:3030-3034]. Because they are sequence-specific, only mRNAs with particular sequences are inactivated.

Investigators have identified two types of ribozymes, *Tetrahymena*-type and "hammerhead"-type. *Tetrahymena*-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to *Tetrahymena*-type ribozymes for inactivating a specific mRNA species and eighteen base recognition sequences are preferable to shorter recognition sequences.

The Bpmp-72 polynucleotide sequences described herein may thus be used to prepare antisense molecules against and ribozymes that cleave mRNAs for Bpmp-72 amino acid sequences, thus inhibiting expression of the Bpmp-72 polynucleotide sequences.

Isolation of Bpmp-72 Polynucleotide Sequences

Any *B. pilosicoli* specimen, in purified or non-purified form, can be utilised as the starting point for the isolation of Bpmp-72 polynucleotide sequences. Such specimens are preferentially extracted from an animal sample, such as blood, tissue material or faeces and the like by a variety of techniques such as those described by Maniatis, et al. in Molecular Cloning: A Laboratory Manual, Cold Spring Harbor, N.Y., p 280-281, (1982).

If the extracted sample has not been purified, it may be treated before isolation of the Bpmp-72 polynucleotide sequence with an amount of a reagent effective to open the cells, or bacterial cell membranes of the sample and to expose and/or separate the strand(s) of the nucleic acid(s).

Once *B. pilosicoli* genomic material has been liberalised there a number of methods by which a Bpmp-72 polynucleotide sequence may be amplified and/or isolated. Details of such methods may be derived from Sambrook et al., (1989) supra or Ausubel et al., (2001) supra.

PCR is perhaps one of the more common approaches that may be used to initially amplify Bpmp-72 polynucleotide sequences and is preferably used in the invention. Specific Bpmp-72 polynucleotide sequences to be amplified may be a fraction of a larger molecule or can be present initially as a discrete molecule, so that the specific sequence constitutes the entire nucleic acid. It is not necessary that the sequence to be amplified is present initially in a pure form; it may be a minor fraction of a complex mixture, such as contained in whole *B. pilosicoli* DNA.

According to the PCR process, deoxyribonucleotide triphosphates dATP, dCTP, dGTP and dTTP are added to the synthesis mixture, either separately or together with the primers, in adequate amounts and the resulting solution is heated to about 90° C.-100° C. from about 1 to 10 minutes, preferably from 1 to 4 minutes. After this heating period, the solution is allowed to cool, which is preferable for the primer hybridisation. To the cooled mixture is added an appropriate agent for effecting the primer extension reaction (called herein "agent for polymerisation"), and the reaction is allowed to occur under conditions known in the art. The agent for polymerisation may also be added together with the other reagents if it is heat stable. This synthesis (or amplification) reaction may occur at room temperature up to a temperature above, which the agent for polymerisation no longer functions. Thus, for example, if DNA polymerase is used as the agent, the temperature is generally no greater than about 40° C. Most conveniently the reaction occurs at room temperature.

The newly synthesised Bpmp-72 strand and its complementary nucleic acid strand will form a double-stranded molecule under hybridising conditions described above and this hybrid is used in subsequent steps of the process.

The steps of denaturing, annealing, and extension product synthesis can be repeated as often as needed to amplify the target Bpmp-72 polynucleotide sequence to the extent necessary for detection. The amount of the specific Bpmp-72 polynucleotide sequence produced will accumulate in an exponential fashion. Such amplification reactions are described in more detail in PCR. A Practical Approach, ILR Press, Eds. M. J. McPherson, P. Quirke, and G. R. Taylor, 1992.

The Bpmp-72 polynucleotide amplification products may be detected by Southern blots analysis, without using radioactive probes. In such a process, for example, a small sample of DNA containing a very low level of the nucleic acid sequence of the Bpmp-72 polynucleotide sequence is amplified and analysed via a Southern blotting technique or similarly, using dot blot analysis. The use of non-radioactive probes or labels is facilitated by the high level of the amplified signal. Alternatively, probes used to detect the amplified products can be directly or indirectly detectably labelled, as described herein.

Sequences amplified by the methods of the invention can be further evaluated, detected, cloned, sequenced and the like, either in solution or after binding to a solid support, by any method usually applied to the detection of a specific DNA sequence such as PCR, oligomer restriction [Saiki, et. al. (1985), Bio/Technology, 3:1008-1012), allele-specific oligonucleotide (ASO) probe analysis [Conner, et. al., (1983) *Proc. Natl. Acad. Sc. U.S.A.,* 80:278], oligonucleotide ligation assays (OLAs) [Landgren, et. al. (1988), *Science,* 241: 1007], and the like.

Alternative methods of amplification have been described and can also be employed in the invention. Such alternative amplification systems include but are not limited to self-sustained sequence replication and nucleic acid sequence-based amplification (which uses reverse transcription and T7 RNA polymerase and incorporates two primers to target its cycling scheme). Alternatively, Bpmp-72 polynucleotide sequence can be amplified by ligation activated transcription or a ligase chain reaction or the repair chain reaction nucleic acid amplification technique.

Bpmp-72 Polynucleotide Constructs and Vectors

According to another embodiment the present invention provides methods for preparing a Bpmp-72 amino acid sequence, comprising the steps of: (a) culturing a cell as described herein under conditions that provide for expression of the Bpmp-72 amino acid sequence; and (b) recovering the expressed Bpmp-72 sequence. This procedure can also be accompanied by the steps of: (c) chromatographing the amino acid sequence using any suitable means known in the art; and/or (d) subjecting the amino acid sequence to protein purification.

To produce a cell capable of expressing Bpmp-72 amino acid sequences, preferably polynucleotide sequences of the invention are incorporated into a recombinant vector, which is then introduced into a host prokaryotic or eukaryotic cell.

Vectors provided by the present invention will typically comprise a Bpmp-72 polynucleotide sequence encoding the desired amino acid sequence and preferably transcription and translational initiation regulatory sequences operably linked to the amino acid encoding sequence. Examples of such expression vectors are described in Sambrook et al., (1989) supra or Ausubel et al., (2001) supra. Many useful vectors are known in the art and may be obtained from such vendors as Stratagene, New England Biolabs, Promega Biotech, and others.

Expression vectors may also include, for example, an origin of replication or autonomously replicating sequence and expression control sequences, a promoter, an enhancer and necessary processing information sites, such as ribosome-binding sites, RNA splice sites, polyadenylation sites, transcriptional terminator sequences, and mRNA stabilising sequences. Secretion signals may also be included where appropriate, from secreted polypeptides of the same or related species, which allow the protein to cross and/or lodge in cell membranes, and thus attain its functional topology, or to be secreted from the cell. Such vectors may be prepared by means of standard recombinant techniques well known in the art and discussed, for example, in Sambrook et al., (1989) supra or Ausubel et al., (2001) supra.

An appropriate promoter and other necessary vector sequences will be selected so as to be functional in the host, and may include, when appropriate, those naturally associated with outer membrane lipoprotein genes.

Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 or promoters derived from murine Moloney leukaemia virus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells that express the inserts. Typical selection genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alanine racemase for *Bacilli*. The choice of the proper selectable marker will depend on the host cell, and appropriate markers for different hosts are well known in the art.

Vectors containing Bpmp-72 polynucleotide sequences can be transcribed in vitro and the resulting RNA introduced into the host cell by well-known methods, e.g., by injection, or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. The introduction of Bpmp-72 polynucleotide sequences into the host cell may be achieved by any method known in the art, including, inter alia, those described above.

The invention also provides host cells transformed or transfected with a Bpmp-72 polynucleotide sequence. Preferred host cells include yeast, filamentous fungi, plant cells, insect, amphibian, avian species, bacteria, mammalian cells, and human cells in tissue culture. Illustratively, such host cells are selected from the group consisting of *E. coli, Pseudomonas, Bacillus, Streptomyces*, yeast, CHO, R1.1, B-W, L-M, COS 1. COS 7, BSC1, BSC40, BMT10, and Sf9 cells.

Large quantities of Bpmp-72 polynucleotide sequence of the invention may be prepared by expressing Bpmp-72 polynucleotide sequences or portions thereof in vectors or other expression vehicles in compatible prokaryotic or eucaryotic host cells. The most commonly used prokaryotic hosts are strains of *Escherichia coli*, although other prokaryotes, such as *Bacillus subtilis* or *Pseudomonas* may also be used. Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate.

Also provided are mammalian cells containing a Bpmp-72 polynucleotide sequences modified in vitro to permit higher expression of Bpmp-72 amino acid sequence by means of a homologous recombinational event consisting of inserting an expression regulatory sequence in functional proximity to the Bpmp-72 amino acid sequence encoding sequence.

Antibodies to the Bpmp-72 Amino Acid Sequence

According to the invention, Bpmp-72 amino acid sequences produced recombinantly or by chemical synthesis and fragments or other derivatives or analogues thereof, including fusion proteins, may be used as an immunogen to generate antibodies that recognize the Bpmp-72 amino acid sequence. Such antibodies include but are not limited to polyclonal, monoclonal, chimeric, single chain, Fab fragments and an Fab expression library.

A molecule is "antigenic" when it is capable of specifically interacting with an antigen recognition molecule of the immune system, such as an immunoglobulin (antibody) or T cell antigen receptor. An antigenic amino acid sequence contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567, as well as antigen binding portions of antibodies, including Fab, $F(ab')_2$ and F(v) (including single chain antibodies). Accordingly, the phrase "antibody molecule" in its various grammatical forms as used herein contemplates both an intact immunoglobulin molecule and an immunologically active portion of an immunoglobulin molecule containing the antibody combining site. An "antibody combining site" is that structural portion of an antibody molecule comprised of heavy and light chain variable and hypervariable regions that specifically binds antigen.

Exemplary antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al., Fab' antibody molecule portions are also well-known and are produced from F(ab')$_2$ portions followed by reduction with mercaptoethanol of the disulfide bonds linking the two heavy chain portions, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The term "adjuvant" refers to a compound or mixture that enhances the immune response to an antigen. An adjuvant can serve as a tissue depot that slowly releases the antigen and also as a lymphoid system activator that non-specifically enhances the immune response [Hood et al., in *Immunology*, p. 384, Second Ed., Benjamin/Cummings, Menlo Park, Calif. (1984)]. Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminium hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (*bacille Calmette-Guerin*) and *Corynebacterium parvum*. Preferably, the adjuvant is pharmaceutically acceptable.

Various procedures known in the art may be used for the production of polyclonal antibodies to Bpmp-72 amino acid sequences, or fragment, derivative or analogues thereof. For the production of antibody, various host animals can be immunised by injection with the Bpmp-72 amino acid sequence, or a derivative (e.g., fragment or fusion protein) thereof, including but not limited to rabbits, mice, rats, sheep, goats, etc. In one embodiment, the Bpmp-72 amino acid sequences or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebacterium parvum.*

For preparation of monoclonal antibodies directed toward the Bpmp-72 amino acid sequences, or fragments, analogues, or derivatives thereof, any technique that provides for the production of antibody molecules by continuous cell lines in culture may be used. These include but are not limited to the hybridoma technique originally developed by Kohler et al., (1975) *Nature,* 256:495-497, the trioma technique, the human B-cell hybridoma technique [Kozbor et al., (1983) *Immunology Today,* 4:72], and the EBV-hybridoma technique to produce human monoclonal antibodies [Cole et al., (1985) in *Monoclonal Antibodies and Cancer Therapy*, pp. 77-96, Alan R. Liss, Inc.]. Immortal, antibody-producing cell lines can be created by techniques other than fusion, such as direct transformation of *B lymphocytes* with oncogenic DNA, or transfection with Epstein-Barr virus. See, e.g., U.S. Pat. Nos. 4,341,761; 4,399,121; 4,427,783; 4,444,887; 4,451,570; 4,466,917; 4,472,500; 4,491,632; and 4,493,890.

In an additional embodiment of the invention, monoclonal antibodies can be produced in germ-free animals utilising recent technology. According to the invention, chicken or swine antibodies may be used and can be obtained by using chicken or swine hybridomas or by transforming B cells with EBV virus in vitro. In fact, according to the invention, techniques developed for the production of "chimeric antibodies" [Morrison et al., (1984) *J. Bacteriol.,* 159-870; Neuberger et al., (1984) *Nature,* 312:604-608; Takeda et al., (1985) *Nature,* 314:452-454] by splicing the genes from a mouse antibody molecule specific for an Bpmp-72 amino acid sequence together with genes from an antibody molecule of appropriate biological activity can be used; such antibodies are within the scope of this invention. Such chimeric antibodies are preferred for use in therapy of intestinal diseases or disorders (described infra), since the antibodies are much less likely than xenogenic antibodies to induce an immune response, in particular an allergic response, themselves.

According to the invention, techniques described for the production of single chain antibodies (U.S. Pat. No. 4,946,778) can be adapted to produce Bpmp-72 amino acid sequence-specific single chain antibodies. An additional embodiment of the invention utilises the techniques described for the construction of Fab expression libraries [Huse et al., (1989) *Science,* 246:1275-1281] to allow rapid and easy identification of monoclonal Fab fragments with the desired specificity for an Bpmp-72 amino acid sequence, or its derivatives, or analogues.

Antibody fragments, which contain the idiotype of the antibody molecule, can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA, "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention. For example, to select antibodies that recognise a specific epitope of a Bpmp-72 amino acid sequence, one may assay generated hybridomas for a product that binds to a Bpmp-72 amino acid sequence fragment containing such epitope. For selection of an antibody specific to a Bpmp-72 amino acid sequence from a particular species of animal, one can select on the basis of positive binding with Bpmp-72 amino acid sequence expressed by or isolated from cells of that species of animal.

Diagnosis

In accordance with another embodiment the invention provides diagnostic and prognostic methods to detect the presence of *Brachyspira* species, including but not limited to *B. hyodysenteriae, B. intermedia, B. alvinipulli, B. aalborgi* and *B. pilosicoli* using Bpmp-72 amino acid sequences and/or antibodies derived there from and/or Bpmp-72 polynucleotide sequences.

Diagnostic and prognostic methods will generally be conducted using a biological sample obtained from an animal, such as chicken or swine. A "sample" refers to a sample of tissue or fluid suspected of containing a *Bachyspira* species, such as *B. pilosicoli* polynucleotide or polypeptide from an animal, but not limited to, e.g., plasma, serum, faecal samples, tissue and samples of in vitro cell culture constituents.

Polypeptide/Antibody-Based Diagnostics

The invention provides methods for detecting the presence of an Bpmp-72 amino acid sequence in a sample, comprising: (a) contacting a sample suspected of containing an Bpmp-72 amino acid sequence with an antibody (preferably bound to a solid support) that specifically binds to the Bpmp-72 amino acid sequence under conditions which allow for the formation of reaction complexes comprising the antibody and the Bpmp-72 amino acid sequence; and (b) detecting the formation of reaction complexes comprising the antibody and Bpmp-72 amino acid sequence in the sample, wherein detection of the formation of reaction complexes indicates the presence of Bpmp-72 amino acid sequence in the sample.

Preferably, the antibody used in this method is derived from an affinity-purified polyclonal antibody, and more preferably a mAb. In addition, it is preferable for the antibody molecules used herein be in the form of Fab, Fab', F(ab')$_2$ or F(v) portions or whole antibody molecules.

Particularly preferred methods for detecting *Brachyspira* species, such as *B. pilosicoli* based on the above method include enzyme linked immunosorbent assays, radioimmunoassays, immunoradiometric assays and immunoenzymatic assays, including sandwich assays using monoclonal and/or polyclonal antibodies.

Three such procedures that are especially useful utilise either the Bpmp-72 amino acid sequence (or a fragment thereof) labelled with a detectable label, antibody Ab$_1$ labelled with a detectable label, or antibody Ab$_2$ labelled with a detectable label. The procedures may be summarized by the following equations wherein the asterisk indicates that the particle is labelled and "AA" stands for the Bpmp-72 amino acid sequence:

$$AA^* + Ab_1 = AA^*Ab_1 \tag{A.}$$

$$AA + Ab^*_1 = AAAb_{1*} \tag{B.}$$

$$AA + Ab_1 + Ab_2^* = Ab_1 AAAb_2^* \tag{C.}$$

The procedures and their application are all familiar to those skilled in the art and accordingly may be utilised within the scope of the present invention. The "competitive" procedure, Procedure A, is described in U.S. Pat. Nos. 3,654,090 and 3,850,752. Procedure B is representative of well-known competitive assay techniques. Procedure C, the "sandwich" procedure, is described in U.S. Pat. No. RE 31,006 and U.S. Pat. No. 4,016,043. Still other procedures are known, such as the "double antibody" or "DASP" procedure.

In each instance, the Bpmp-72 amino acid sequences form complexes with one or more antibody(ies) or binding partners and one member of the complex is labelled with a detectable label. The fact that a complex has formed and, if desired, the amount thereof, can be determined by known methods applicable to the detection of labels.

It will be seen from the above, that a characteristic property of Ab$_2$ is that it will react with Ab$_1$. This is because Ab$_1$, raised in one mammalian species, has been used in another species as an antigen to raise the antibody, Ab$_2$. For example, Ab$_2$ may be raised in goats using rabbit antibodies as antigens. Ab$_2$ therefore would be anti-rabbit antibody raised in goats. For purposes of this description and claims, Ab$_1$ will be referred to as a primary antibody, and Ab$_2$ will be referred to as a secondary or anti-Ab$_1$ antibody.

The labels most commonly employed for these studies are radioactive elements, enzymes, chemicals that fluoresce when exposed to ultraviolet light, and others.

A number of fluorescent materials are known and can be utilised as labels. These include, for example, fluorescein, rhodamine and auramine. A particular detecting material is anti-rabbit antibody prepared in goats and conjugated with fluorescein through an isothiocyanate.

The Bpmp-72 amino acid sequence or their binding partners can also be labelled with a radioactive element or with an enzyme. The radioactive label can be detected by any of the currently available counting procedures. The preferred isotope may be selected from $^3$H, $^{14}$C, $^{32}$P, $^{35}$S, $^{36}$Cl, $^{51}$Cr $^{57}$Co, $^{58}$Co, $^{59}$Fe, $^{90}$Y, $^{125}$I, $^{131}$I, and $^{185}$Re.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes, which can be used in these procedures, are known and can be utilized. The preferred enzymes are peroxidase, β-glucuronidase, β-D-glucosidase, β-D-galactosidase, urease, glucose oxidase plus peroxidase and alkaline phosphatase. U.S. Pat. Nos. 3,654,090, 3,850,752 and 4,016,043 are referred to by way of example for their disclosure of alternate labelling material and methods.

The invention also provides a method of detecting intestinal spirochaetosis antibodies in biological samples, which comprises: (a) providing a Bpmp-72 amino acid sequence or a fragment thereof; (b) incubating a biological sample with said amino acid sequence under conditions which allow for the formation of an antibody-antigen complex; and (c) determining whether an antibody-antigen complex comprising said amino acid sequence is formed.

In another embodiment of the invention there are provided in vitro methods for evaluating the level of Bpmp-72 antibodies in a biological sample comprising: (a) detecting the formation of reaction complexes in a biological sample according to the method noted above; and (b) evaluating the amount of reaction complexes formed, which amount of reaction complexes corresponds to the level of Bpmp-72 antibodies in the biological sample.

Further there are provided in vitro methods for monitoring therapeutic treatment of a disease associated with *Brachyspira* species, including but not limited to *B. hyodysenteriae, B. intermedia, B. alvinipulli, B. aalborgi* and *B. pilosicoli* in an animal host comprising evaluating, as describe above, the levels of Bpmp-72 antibodies in a series of biological samples obtained at different time points from an animal host undergoing such therapeutic treatment.

Nucleic Acid-Based Diagnostics

The present invention further provides methods for detecting the presence or absence of *Brachyspira* species, including but not limited to *B. hyodysenteriae, B. intermedia, B. alvinipulli, B. aalborgi* and *B. pilosicoli* in a biological sample, which comprise the steps of: (a) bringing the biological sample into contact with a polynucleotide probe or primer comprising a Bpmp-72 polynucleotide of the invention under suitable hybridising conditions; and (b) detecting any duplex formed between the probe or primer and nucleic acid in the sample.

According to one embodiment of the invention, detection of *Brachyspira* species, such as *B. pilosicoli* may be accomplished by directly amplifying Bpmp-72 polynucleotide sequences from biological sample, using known techniques and then detecting the presence of Bpmp-72 polynucleotide sequences.

In one form of the invention, the target nucleic acid sequence is amplified by PCR and then detected using any of the specific methods mentioned above. Other useful diagnostic techniques for detecting the presence of Bpmp-72 polynucleotide sequences include, but are not limited to: 1) allele-specific PCR; 2) single stranded conformation analysis; 3) denaturing gradient gel electrophoresis; 4) RNase protection assays; 5) the use of proteins which recognize nucleotide mismatches, such as the *E. coli* mutS protein; 6) allele-specific oligonucleotides; and 7) fluorescent in situ hybridisation.

In addition to the above methods Bpmp-72 polynucleotide sequences may be detected using conventional probe technology. When probes are used to detect the presence of the Bpmp-72 polynucleotide sequences, the biological sample to be analysed, such as blood or serum, may be treated, if desired, to extract the nucleic acids. The sample polynucleotide sequences may be prepared in various ways to facilitate detection of the target sequence; e.g. denaturation, restriction digestion, electrophoresis or dot blotting. The targeted region of the sample polynucleotide sequence usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Sample polynucleotide sequences and probes are incubated under conditions that promote stable hybrid formation of the target sequence in the probe with the putative Bpmp-72 polynucleotide sequence in the sample. Preferably, high stringency conditions are used in order to prevent false positives.

Detection, if any, of the resulting hybrid is usually accomplished by the use of labelled probes. Alternatively, the probe may be unlabeled, but may be detectable by specific binding with a ligand that is labelled, either directly or indirectly. Suitable labels and methods for labelling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labelled moiety.

It is also contemplated within the scope of this invention that the nucleic acid probe assays of this invention may employ a cocktail of nucleic acid probes capable of detecting Bpmp-72 polynucleotide sequences. Thus, in one example to detect the presence of Bpmp-72 polynucleotide sequences in a cell sample, more than one probe complementary to Bpmp-72 polynucleotide sequences is employed and in particular the number of different probes is alternatively 2, 3, or 5 different nucleic acid probe sequences.

Nucleic Acid Arrays—"DNA Chip" Technology

Bpmp-72 polynucleotide sequences (preferably in the form of probes) may also be immobilised to a solid phase support for the detection of *Brachyspira* species, including but not limited to *B. hyodysenteriae, B. intermedia, B. alvinipulli, B. aalborgi* and *B. pilosicoli*. Alternatively the Bpmp-72 polynucleotide sequences will form part of a library of DNA molecules that may be used to detect simultaneously a number of different genes from *Brachyspira* species, such as *B. pilosicoli*. In a further alternate form of the invention Bpmp-72 polynucleotide sequences together with other polynucleotide sequences (such as from other bacteria or viruses) may be immobilised on a solid support in such a manner permitting identification of the presence of a *Brachyspira* species, such as *B. pilosicoli* and/or any of the other polynucleotide sequences bound onto the solid support.

Techniques for producing immobilised libraries of DNA molecules have been described in the art. Generally, most prior art methods describe the synthesis of single-stranded nucleic acid molecule libraries, using for example masking techniques to build up various permutations of sequences at the various discrete positions on the solid substrate. U.S. Pat. No. 5,837,832 describes an improved method for producing DNA arrays immobilised to silicon substrates based on very large scale integration technology. In particular, U.S. Pat. No. 5,837,832 describes a strategy called "tiling" to synthesize specific sets of probes at spatially defined locations on a substrate that may be used to produced the immobilised DNA libraries of the present invention. U.S. Pat. No. 5,837,832 also provides references for earlier techniques that may also be used. Thus polynucleotide sequence probes may be synthesised in situ on the surface of the substrate.

Alternatively, single-stranded molecules may be synthesised off the solid substrate and each pre-formed sequence applied to a discrete position on the solid substrate. For example, polynucleotide sequences may be printed directly onto the substrate using robotic devices equipped with either pins or pizo electric devices.

The library sequences are typically immobilised onto or in discrete regions of a solid substrate. The substrate may be porous to allow immobilisation within the substrate or substantially non-porous, in which case the library sequences are typically immobilised on the surface of the substrate. The solid substrate may be made of any material to which polypeptides can bind, either directly or indirectly. Examples of suitable solid substrates include flat glass, silicon wafers, mica, ceramics and organic polymers such as plastics, including polystyrene and polymethacrylate. It may also be possible to use semi-permeable membranes such as nitrocellulose or nylon membranes, which are widely available. The semi-permeable membranes may be mounted on a more robust solid surface such as glass. The surfaces may optionally be coated with a layer of metal, such as gold, platinum or other transition metal. A particular example of a suitable solid substrate is the commercially available BiaCore™ chip (Pharmacia Biosensors).

Preferably, the solid substrate is generally a material having a rigid or semi-rigid surface. In preferred embodiments, at least one surface of the substrate will be substantially flat, although in some embodiments it may be desirable to physically separate synthesis regions for different polymers with, for example, raised regions or etched trenches. It is also preferred that the solid substrate is suitable for the high density application of DNA sequences in discrete areas of typically from 50 to 100 µm, giving a density of 10000 to 40000 dots/cm$^{-2}$.

The solid substrate is conveniently divided up into sections. This may be achieved by techniques such as photoetching, or by the application of hydrophobic inks, for example teflon-based inks (Cel-line, USA).

Discrete positions, in which each different member of the library is located may have any convenient shape, e.g., circular, rectangular, elliptical, wedge-shaped, etc.

Attachment of the polynucleotide sequences to the substrate may be by covalent or non-covalent means. The polynucleotide sequences may be attached to the substrate via a layer of molecules to which the library sequences bind. For example, the polynucleotide sequences may be labelled with biotin and the substrate coated with avidin and/or streptavidin. A convenient feature of using biotinylated polynucleotide sequences is that the efficiency of coupling to the solid substrate can be determined easily. Since the polynucleotide sequences may bind only poorly to some solid substrates, it is often necessary to provide a chemical interface between the solid substrate (such as in the case of glass) and the nucleic acid sequences. Examples of suitable chemical interfaces include hexaethylene glycol. Another example is the use of polylysine coated glass, the polylysine then being chemically modified using standard procedures to introduce an affinity ligand. Other methods for attaching molecules to the surfaces of solid substrate by the use of coupling agents are known in the art, see for example WO98/49557.

Binding of complementary polynucleotide sequences to the immobilised nucleic acid library may be determined by a variety of means such as changes in the optical characteristics of the bound polynucleotide sequence (i.e. by the use of ethidium bromide) or by the use of labelled nucleic acids, such as polypeptides labelled with fluorophores. Other detection techniques that do not require the use of labels include optical techniques such as optoacoustics, reflectometry, ellipsometry and surface plasmon resonance (see WO97/49989).

Thus, the present invention provides a solid substrate having immobilized thereon at least one polynucleotide of the present invention, preferably two or more different polynucleotide sequences of the present invention. In a preferred embodiment the solid substrate further comprises polynucleotide sequences derived from genes other than the Bpmp-72 polynucleotide sequence.

Therapeutic Uses

The present invention also can be used as a prophylactic or therapeutic, which may be utilised for the purpose of stimulating humoral and cell mediated responses in animals, such as chickens and swine, thereby providing protection against colonisation with *Brachyspira* species, including but not limited to *B. hyodysenteriae, B. intermedia, B. alvinipulli, B. aalborgi* and *B. pilosicoli*. Natural infection with a *Brachyspira* species, such as *B. pilosicoli* induces circulating antibody titres against Bpmp-72. Therefore, Bpmp-72 amino acid sequence or parts thereof, have the potential to form the basis of a systemically or orally administered prophylactic or therapeutic to provide protection against intestinal spirochaetosis.

Accordingly, in one embodiment the present invention provides Bpmp-72 amino acid sequence or fragments thereof or antibodies that bind said amino acid sequences or the polynucleotide sequences described herein in a therapeutically effective amount admixed with a pharmaceutically acceptable carrier, diluent, or excipient.

The phrase "therapeutically effective amount" is used herein to mean an amount sufficient to reduce by at least about 15%, preferably by at least 50%, more preferably by at least 90%, and most preferably prevent, a clinically significant deficit in the activity, function and response of the animal host. Alternatively, a therapeutically effective amount is sufficient to cause an improvement in a clinically significant condition in the animal host.

The phrase "pharmaceutically acceptable" refers to molecular entities and compositions that are physiologically tolerable and do not typically produce an allergic or similarly untoward reaction, such as gastric upset and the like, when administered to an animal. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or saline solutions and aqueous dextrose and glycerol solutions are preferably employed as carriers, particularly for injectable solutions. Suitable pharmaceutical carriers are described in Martin, *Remington's Pharmaceutical Sciences*, 18th Ed., Mack Publishing Co., Easton, Pa., (1990).

In a more specific form of the invention there are provided pharmaceutical compositions comprising therapeutically effective amounts of Bpmp-72 amino acid sequence or a analogue, fragment or derivative product thereof or antibodies thereto together with pharmaceutically acceptable diluents, preservatives, solubilizes, emulsifiers, adjuvants and/or carriers. Such compositions include diluents of various buffer content (e.g., Tris-HCl, acetate, phosphate), pH and ionic strength and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The material may be incorporated into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., *Martin, Remington's Pharmaceutical Sciences,* 18th Ed. (1990, Mack Publishing Co., Easton, Pa. 18042) pages 1435-1712 that are herein incorporated by reference. The compositions may be prepared in liquid form, or may be in dried powder, such as lyophilised form.

Administration

It will be appreciated that pharmaceutical compositions provided accordingly to the invention may be administered by any means known in the art. Preferably, the pharmaceutical compositions for administration are administered by injection, orally, or by the pulmonary, or nasal route. The Bpmp-72 amino acid sequence or antibodies derived there from are more preferably delivered by intravenous, intraarterial, intraperitoneal, intramuscular, or subcutaneous routes of administration. Alternatively, the Bpmp-72 amino acid sequence or antibodies derived there from, properly formulated, can be administered by nasal or oral administration.

Polynucleotide Base Therapy

Also addressed by the present invention is the use of polynucleotide sequences of the invention, as well as antisense and ribozyme polynucleotide sequences hybridisable to a polynucleotide sequence encoding an Bpmp-72 amino acid sequence according to the invention, for manufacture of a medicament for modulation of a disease associated *B. pilosicoli*.

Polynucleotide sequences encoding antisense constructs or ribozymes for use in therapeutic methods are desirably administered directly as a naked nucleic acid construct. Uptake of naked nucleic acid constructs by bacterial cells is enhanced by several known transfection techniques, for example those including the use of transfection agents. Example of these agents include cationic agents (for example calcium phosphate and DEAE-dextran) and lipofectants (for example lipofectam™ and transfectam™). Typically, nucleic acid constructs are mixed with the transfection agent to produce a composition.

Alternatively the antisense construct or ribozymes may be combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, intraocular, oral or transdermal administration.

The routes of administration described are intended only as a guide since a skilled practitioner will be able to determine readily the optimum route of administration and any dosage for any particular animal and condition.

Drug Screening Assays

The present invention also provides assays that are suitable for identifying substances that bind to Bpmp-72 amino acid sequences. In addition, assays are provided that are suitable for identifying substances that interfere with Bpmp-72 amino acid sequences. Assays are also provided that test the effects of candidate substances identified in preliminary in vitro assays on intact cells in whole cell assays.

One type of assay for identifying substances that bind to Bpmp-72 amino acid sequences involves contacting an Bpmp-72 amino acid sequence, which is immobilised on a solid support, with a non-immobilised candidate substance and determining whether and/or to what extent the Bpmp-72 amino acid sequences and candidate substance bind to each other. Alternatively, the candidate substance may be immobilised and the Bpmp-72 amino acid sequence non-immobilised.

In a preferred assay method, the Bpmp-72 amino acid sequence is immobilised on beads such as agarose beads. Typically this is achieved by expressing the component as a GST-fusion protein in bacteria, yeast or higher eukaryotic cell lines and purifying the GST-fusion protein from crude cell extracts using glutathione-agarose beads. The binding of the candidate substance to the immobilised Bpmp-72 amino acid sequence is then determined. This type of assay is known in the art as a GST pulldown assay. Again, the candidate substance may be immobilised and the Bpmp-72 amino acid sequence non-immobilised.

It is also possible to perform this type of assay using different affinity purification systems for immobilising one of the components, for example Ni-NTA agarose and hexahistidine-tagged components.

Binding of the Bpmp-72 amino acid sequence to the candidate substance may be determined by a variety of methods well known in the art. For example, the non-immobilised component may be labelled (with for example, a radioactive label, an epitope tag or an enzyme-antibody conjugate). Alternatively, binding may be determined by immunological detection techniques. For example, the reaction mixture can be Western blotted and the blot probed with an antibody that detects the non-immobilised component. ELISA techniques may also be used.

Candidate substances are typically added to a final concentration of from 1 to 1000 nmol/ml, more preferably from 1 to 100 nmol/ml. In the case of antibodies, the final concentration used is typically from 100 to 500 μg/ml, more preferably from 200 to 300 μg/ml.

Thus, the present invention provides methods of screening for drugs comprising contacting such an agent with a Bpmp-72 amino acid sequence or fragment thereof and assaying (i) for the presence of a complex between the agent and the Bpmp-72 amino acid sequence or fragment, or (ii) for the presence of a complex between the Bpmp-72 amino acid sequence or fragment and a ligand, by methods well known in the art. In such competitive binding assays the Bpmp-72 amino acid sequence or fragment is typically labelled. Free Bpmp-72 amino acid sequence or fragment is separated from that present in a protein:protein complex, and the amount of free (i.e., uncomplexed) label is a measure of the binding of the agent being tested to the Bpmp-72 amino acid sequence or its interference with Bpmp-72 amino acid sequence:ligand binding, respectively.

Another technique for drug screening provides high throughput screening for compounds having suitable binding affinity to the Bpmp-72 amino acid sequence and is described in detail in Geysen, PCT published application WO 84/03564, published on Sep. 13, 1984. Briefly stated, large numbers of different small peptide test compounds are synthesised on a solid substrate, such as plastic pins or some other surface. The peptide test compounds are reacted with Bpmp-72 amino acid sequence and washed. Bound Bpmp-72 amino acid sequence is then detected by methods well known in the art.

This invention also contemplates the use of competitive drug screening assays in which antibodies capable of specifically binding the Bpmp-72 amino acid sequence compete with a test compound for binding to the Bpmp-72 amino acid sequence or fragments thereof. In this manner, the antibodies can be used to detect the presence of any peptide that shares one or more antigenic determinants of the Bpmp-72 amino acid sequence.

Kits

The invention also provides kits for screening animals suspected of being infected with a *Brachyspira* species, such as *B. pilosicoli* or to confirm that an animal is infected with a *Braqchyspira* species, such as *B. pilosicoli*, which kit comprises at least a polynucleotide sequence complementary to a portion of the Bpmp-72 polynucleotide sequence, packaged in a suitable container, together with instructions for its use.

In a further embodiment of this invention, kits suitable for use by a specialist may be prepared to determine the presence or absence of Brachyspira species, including but not limited to B. hyodysenteriae, B. intermedia, B. alvinipulli, B. aalborgi and B. pilosicoli in suspected infected animals or to quantitatively measure a Brachyspira species, including but not limited to B. hyodysenteriae, B. intermedia, B. alvinipulli, B. aalborgi and B. pilosicoli infection. In accordance with the testing techniques discussed above, one class of such kits will contain at least the labelled Bpmp-72 amino acid sequence or its binding partner, for instance an antibody specific thereto, and directions depending upon the method selected, e.g., "competitive," "sandwich," "DASP" and the like. The kits may also contain peripheral reagents such as buffers, stabilizers, etc.

Accordingly, a test kit may be prepared for the demonstration of the presence of a Brachyspira species, including but not limited to B. hyodysenteriae, B. intermedia, B. alvinipulli, B. aalborgi and B. pilosicoli, comprising:

(a) a predetermined amount of at least one labelled immunochemically reactive component obtained by the direct or indirect attachment of the present Bpmp-72 amino acid sequence or a specific binding partner thereto, to a detectable label;
(b) other reagents; and
(c) directions for use of said kit.

More specifically, the diagnostic test kit may comprise:

(a) a known amount of the Bpmp-72 amino acid sequence as described above (or a binding partner) generally bound to a solid phase to form an immunosorbent, or in the alternative, bound to a suitable tag, or there are a plural of such end products, etc;
(b) if necessary, other reagents; and
(c) directions for use of said test kit.

In a further variation, the test kit may be prepared and used for the purposes stated above, which operates according to a predetermined protocol (e.g. "competitive," "sandwich," "double antibody," etc.), and comprises:

(a) a labelled component which has been obtained by coupling the Bpmp-72 amino acid sequence to a detectable label;
(b) one or more additional immunochemical reagents of which at least one reagent is a ligand or an immobilized ligand, which ligand is selected from the group consisting of:
    (i) a ligand capable of binding with the labelled component (a);
    (ii) a ligand capable of binding with a binding partner of the labelled component (a);
    (iii) a ligand capable of binding with at least one of the component(s) to be determined; or
    (iv) a ligand capable of binding with at least one of the binding partners of at least one of the component(s) to be determined; and
(c) directions for the performance of a protocol for the detection and/or determination of one or more components of an immunochemical reaction between the Bpmp-72 amino acid sequence and a specific binding partner thereto.

BEST MODE(S) FOR CARRYING OUT THE INVENTION

Further features of the present invention are more fully described in the following non-limiting Examples. It is to be understood, however, that this detailed description is included solely for the purposes of exemplifying the present invention. It should not be understood in any way as a restriction on the broad description of the invention as set out above.

Methods of molecular cloning, immunology and protein chemistry, which are not explicitly described in the following examples, are reported in the literature and are known by those skilled in the art. General texts that described conventional molecular biology, microbiology, and recombinant DNA techniques within the skill of the art, included, for example: Sambrook et al., *Molecular Cloning: A Laboratory Manual*, Second Edition, Cold Spring Harbor Laboratory Press, Cold Spring Harbor, N.Y. (1989); Glover ed., *DNA Cloning: A Practical Approach*, Volumes I and II, MRL Press, Ltd., Oxford, U.K. (1985); and Ausubel, F., Brent, R., Kingston, R. E., Moore, D. D., Seidman, J. G., Smith, J. A., Struhl, K. *Current protocols in molecular biology*. Greene Publishing Associates/Wiley Intersciences, New York (2001).

EXAMPLE 1

Identification and Characterisation of the Gene Encoding a 72 kDa Outer-Envelope Protein of *Brachyspira pilosicoli*

Methods

Production of Polyclonal Antibody (AHPS) for Screening

Serum (1.0 ml) from a pig hyper-immunised with *Brachyspira pilosicoli* strain 1648 was added to a cell suspension (9.0 ml) containing $10^{12}$ cells of Brachyspira hyodysenteriae B78$^T$, Brachyspira intermedia PWS/A$^T$, Brachyspira innocens B$_{256}$$^T$, Brachyspira murdochii 56-150$^T$, Brachyspira aalborgi 513$^T$ and *Escherichia coli* JM109. The slurry was incubated at 4° C. overnight with continuous end-to-end mixing. Antibodies which had absorbed onto the cells were removed by centrifugation at 5,000×g for 20 minutes at 4° C. The supernatant was removed and used to resuspend a combined cell pellet containing $10^{12}$ cells of B. hyodysenteriae B78$^T$, B. intermedia PWS/A$^T$, B. innocens B256$^T$, B. murdochii 56-150$^T$, B. aalborgi 513$^T$ and E. coli JM109. The slurry was incubated at 4° C. overnight with continuous end-to-end mixing. The antibodies which had absorbed onto the cells were again removed by centrifugation at 5,000×g for 20 minutes at 4° C. The process of absorption was repeated a further two times. After the final absorption, the absorbed hyper-immune pig serum (AHPS) was divided into (50 µl) aliquots and stored at −80° C.

Screening of the Genomic Library

A B. pilosicoli P43/6178 genomic library was generated by ligating partially-restricted high molecular weight DNA (2-3 kb) into lambda bacteriophage arms and packaging the phage particles using Gigapack II extracts (Stratagene). The resulting phage library was amplified in E. coli and immuno-screened with diluted AHPS using the standard plaque-lift method. Four clones (designated AHP1-4) were excised into plasmids following three rounds of immuno-screening.

Expression of the Gene Encoding the 72 kDa Outer-Membrane Protein (Bpmp-72) in E. coli The E. coli clones harbouring the recombinant plasmids were streaked out onto LB agar plates supplemented with kanamycin (50 mg/L) and incubated at 37° C. overnight. A single colony was used to inoculate LB broth (10 ml) supplemented with kanamycin (50 mg/l), PMSF (1 mM) and IPTG (1 mM). The broth culture was incubated at 37° C. for 12 h with shaking. An aliquot of each culture (1.0 ml) was centrifuged at 2,500×g for 15 minutes and washed three times. The washing process involved re-suspension of the cell pellet with phosphate buffered saline (PBS) (1 ml) and centrifugation at 2,500×g for 15 minutes. The washed cell pellets were resuspended in PBS (100 μl) in preparation for sodium dodecyl sulfate polyacrylamide gel electrophoresis (SDS-PAGE) and Western blotting.

SDS Polyacrylamide Gel Electrophoresis of Bpmp-72 Proteins

SDS-PAGE analysis of protein involved electrophoretic separation using a discontinuous Tris-glycine buffer system. Aliquots of protein sample (30 μl) were mixed with 10 μl of 4× sample treatment buffer (250 mM Tris-HCl (pH 6.0), 8% (w/v) SDS, 200 mM DTT, 40% (v/v) glycerol and 0.04% (w/v) bromophenol blue). Samples were boiled for 5 minutes immediately prior to loading the sample (10 μl) into wells in the gel. The gel comprised a stacking gel (125 mM Tris-HCl ph 6.8, 4% w/v acylamide, 0.15% w/v bis-acrylamide and 0.1% w/v SDS) and a separating gel (375 mM Tris-HCl ph 8.8, 12% w/v acylamide, 0.31% w/v bis-acrylamide and 0.1% w/v SDS). These gels were polymerised by the addition of 0.1% (v/v) TEMED and 0.05% (w/v) freshly prepared ammonium sulphate solution and cast into the mini-Protean dual slab cell (Bio-Rad). Samples were run at 150 V at room temperature (RT) until the bromophenol blue dye-front reached the bottom of the gel. Pre-stained molecular weight standards were electrophoresed in parallel with the samples in order to allow molecular weight estimations. After electrophoresis, the gel was immediately subjected to electro-transfer onto nitrocellulose membrane for Western blotting.

Western Blot Analysis

Electrophoretic transfer of separated proteins from the SDS-PAGE gel to nitrocellulose membrane was performed using the Towbin transfer buffer system. After electrophoresis, the gel was equilibrated in transfer buffer (25 mM Tris, 192 mM glycine, 20% v/v methanol, pH 8.3) for 15 minutes. The proteins in the gel were transferred to nitrocellulose membrane (Protran) using the mini-Protean transblot apparatus (Bio-Rad). After assembly of the gel holder according to the manufacturer's instructions, electrophoretic transfer was performed at 30 V overnight at 4° C. The freshly transferred nitrocellulose membrane containing the separated proteins was blocked with 10 ml of Tris-buffered saline (TBS) containing 5% (w/v) skim milk powder for 1 hour at room temperature. The membrane was washed with TBS (0.1% (v/v) Tween 20 (TBST)) and then incubated with 10 mL AHPS (diluted 5,000-fold with TBST) for 1 hour at room temperature. After washing three times for 5 minutes with TBST, the membrane was incubated with 10 mL goat anti-swine IgG (whole molecule)-HRP diluted 5,000-fold in TBST for 1 hour at room temperature. The membrane was developed with 10 mL of DAB substrate solution (0.5 mg/ml 3,3'-diaminobenzidine, 0.003% w/v hydrogen peroxide, TBS). The development reaction was stopped by washing the membrane with distilled water. The membrane was then dried and scanned for presentation.

Sequencing of the B. pilosicoli Insert

The plasmid AHP1 was chosen for direct sequencing of the B. pilosicoli genomic insert using the ABI 373A DNA Sequencer (PE Applied Biosystems). The phagemid was purified from the E. coli cells using the QIAprep Spin Miniprep Kit (Qiagen) according to the manufacturer's instructions. The initial insert sequences were obtained using commercially available T3 and T7 oligonucleotides which annealed to the vector regions flanking either ends of the insert. The remaining oligonucleotides were designed based on the 3'-OH end of the upstream insert sequences (Table 2). "$T_A$" indicates the optimised annealing temperature for the PCR using the oligonucleotide.

TABLE 2

| Primer name | $T_A$ (° C.) | Sequence (5'-3') | SEQ ID NO: |
|---|---|---|---|
| T3 | 60 | TAA CCC TCA CTA AAG GGA AC | 23 |
| AHP-F1 | 50 | TGA ATG CTA TAG AAG AGA GAG GAC | 24 |
| T7 | 60 | GTA ATA CGA CTC ACT ATA GGG C | 25 |

Each sequencing reaction was performed in an aliquot (10 μl) of phagemid (300 ng), of primer (4 pmol), and ABI PRISM™ Dye Terminator Cycle Sequencing Ready Reaction Mix (4 μl) (PE Applied Biosystems). Cycling conditions involved a 2 minute denaturing step at 96° C., followed by 25 cycles of denaturation at 96° C. for 10 seconds, annealing at the primer's melting temperature (Table 2) for 5 seconds, and primer extension at 60° C. for 4 minutes. Residual dye terminators were removed from the sequencing products by precipitation with 95% (v/v) ethanol containing 120 mM sodium acetate (pH 4.6), and vacuum dried. The sequencing products were analysed using an ABI 373A DNA Sequencer.

Completion of the Bpmp-72 Sequence

Cloning of Genomic DNA Fragments into a Sequencing Vector

Purified chromosomal DNA from B. pilosicoli P43/6178 was digested to completion using HinDIII. Briefly, chromosomal DNA (2 μg) and pTrcHis plasmid (1 μg) (Invitrogen) were incubated separately at 37° C. overnight in 1× HinDIII buffer containing 20 U of HinDIII (New England Biolabs). The restriction products were purified using the UltraClean PCR Clean-up Kit (Mo Bio Laboratories), according to the manufacturer's instructions. An aliquot of linearised pTrcHis vector (100 ng) was incubated with restricted B. pilosicoli genomic DNA (100 ng) at 14° C. for 16 hours in 30 mM Tris-HCl (pH 7.8), 10 mM MgCl$_2$, 10 mM DTT and 1 mM ATP containing 1 U of T4 DNA ligase (Promega). The product of this ligation reaction was designated pTrc-PIL. An identical ligation reaction containing no genomic DNA was also included as a vector re-circularisation negative control. All ligation reactions were all performed in a total volume of 20 μl.

Polymerase Chain Reaction (PCR) Amplification of Ligated DNA

The primers used were pTrcHis-F (5'-CAATTTATCAGA-CAATCTGTGTG-3') (SEQ ID NO: 26) which anneals to the complementary sequences flanking the HinDIII cloning site of pTrcHis, and AHP-Rev (5'-TCGCTTGCAGTTTGAG-GAGTG-3') (SEQ ID NO: 27) which anneals to the complementary sequences at the 5'-terminus of the B. pilosicoli partial ORF. The ligated DNA was amplified by PCR in a 50 μl total volume using Taq DNA polymerase (Biotech International) and Pfu DNA polymerase (Promega). The amplification mixture consisted of 1× PCR buffer (containing 1.5 mM of MgCl$_2$), 0.5 U of Taq DNA polymerase, 0.05 U Pfu DNA polymerase, 0.2 mM of each dNTP (Amersham Pharmacia Biotech), 0.5 μM of the primer pair (pTrcHis-F, AHP-Rev), and pTrc-PIL (2 μl). Cycling conditions involved an initial template denaturation step of 5 minutes at 94° C., followed by 30 cycles of denaturation at 94° C. for 30 seconds, annealing at 55° C. for 15 seconds, and primer extension at 68° C. for 4 minutes. The PCR products were subjected to electrophoresis in 1.5% (w/v) agarose gels in 1×TAE buffer (40 mM Tris-acetate, 1 mM EDTA), stained with an ethidium bromide solution (1 μg/ml) and viewed using UV light.

Sequencing of the ORF Extension for Bpmp-72

Amplification products from the PCR of pTrc-PIL were purified using the UltraClean PCR Clean-up Kit according to the manufacturer's instructions. Sequencing of the PCR product was performed in duplicate using the pTrcHis-F and AHP-Rev primers. Each sequencing reaction was performed in a 10 µl volume consisting of PCR product (50 ng), primer (2 pmol), and the ABI PRISM™ Dye Terminator Cycle Sequencing Ready Reaction Mix (4 µl) (PE Applied Biosystems). Cycling conditions involved a 2 minute denaturing step at 96° C., followed by 25 cycles of denaturation at 96° C. for 10 seconds, primer annealing at 55° C. for 5 seconds 120 mM sodium acetate (pH 4.6), and vacuum dried. The sequencing products were analysed using an ABI 373A DNA Sequencer. Sequence results were edited, compiled and compared using SeqEd v1.0.3 and Vector NTI version 6.

Sequencing of the Remaining ORF for Bpmp-72

PCR amplification of the pTrc-PIL was repeated as above. The primers used were pTrcHis-F and AHP-Rev2 (5'-TGGATTTTGMGCTATTGCTC-3') (SEQ ID NO: 28). SEQ ID NO:28 anneals to the complementary sequences at the 5'-terminus of the extended B. pilosicoli partial ORF. Sequencing of the remaining unknown region of the Bpmp-72 ORF was performed as previously described using the pTrcHis-F and AHP-Rev2 primers. The sequencing products were analysed using an ABI 373A DNA Sequencer. Sequence results were edited, compiled and compared using SeqEd v1.0.3 and Vector NTI version 6.

Analysis of the Hypothetical Bpmp-72 ORF

Sequence results were edited and compiled using SeqEd v1.0.3 (PE Applied Biosystems). The nucleotide sequences were analysed using Vector NTI version 6 (InforMax) and the University of Wisconsin Genetics Computer Group program. The deduced hypothetical open reading frame (ORF) was used to search for homology against all sequence databases available at the National Center of Bioinformatics (NCBI).

Polymerase Chain Reaction (PCR) Analysis of Bpmp-72 in *Brachyspira* spp.

Two primers which annealed to the 913 and 1692 bp region of the Bpmp-72 ORF were designed and optimised for PCR detection of the gene encoding the 72 kDa outer-membrane protein from 82 Brachyspiral genomic DNA: 48 strains of *B. hyodysenteriae*, 18 strains of *B. pilosicoli*, 12 strains of *B. intermedia*, 8 strains of *B. murdochii*, 4 strains of *B. innocens*, 2 strains of "Brachyspira canis", 1 strain of *Brachyspira alvinipulli* and 1 strain of *B. aalborgi*. The primers used were AHP-F4 (5'-CAAGTAATAGCTAAAGGTGATG-3') (SEQ ID NO:29) and AHP-R783 (5'-TTACTGTTGTGCTTGAGTAGTG-3') (SEQ ID NO:30) which anneal to complementary sequences flanking the *B. pilosicoli* ORF. The gene was amplified by PCR in a 50 µl total volume using Taq DNA polymerase (Biotech International) and Pfu DNA polymerase (Promega). The amplification mixture consisted of 1× PCR buffer (containing 1.5 mM of MgCl$_2$), 0.5 U of Taq DNA polymerase, 0.05 U Pfu DNA polymerase, 0.2 mM of each dNTP (Amersham Pharmacia Biotech), 0.5 µM of the primer pair (AHP-F4, AHP-R783), and 2.5 µl purified chromosomal template DNA. Cycling conditions involved an initial template denaturation step of 5 minutes at 94° C., followed by 30 cycles of denaturation at 94° C. for 30 seconds, annealing at 55° C. for 15 seconds, and primer extension at 68° C. for 2 minutes. The PCR products were subjected to electrophoresis in 1.5% (w/v) agarose gels in 1× TAE buffer (40 mM Tris-acetate, 1 mM EDTA), stained with a solution of ethidium bromide (1 µg/ml) and viewed using UV light.

Sequencing of Bpmp-72 Present in Other *B. pilosicoli* Strains

PCR of Bpmp-72 from *B. pilosicoli* Strains

Two primers which annealed 98 base pairs upstream to the Bpmp-72 ORF, AHP-98F (5'-CGTTTAGCTGAACTTGAAGCTATG-3') (SEQ ID NO: 31) and 178 base pairs downstream from the ORF, AHP+1890R (5'-GTAATGCTCTGTCTTAATCAT-3') (SEQ ID NO: 32) were designed and optimised for PCR amplification of Bpmp-72 for sequencing templates. The PCR was performed in a 50 µl total volume using Taq DNA polymerase (Biotech International) and Pfu DNA polymerase (Promega). The amplification mixture consisted of 1× PCR buffer (containing 1.5 mM of MgCl$_2$), 0.5 U of Taq DNA polymerase, 0.05 U Pfu DNA polymerase, 0.2 mM of each dNTP (Amersham Pharmacia Biotech), 0.5 µM of the primer pair (AHP-L1, AHP-R1), and 2.5 µl purified chromosomal template DNA. Cycling conditions involved an initial template denaturation step of 5 minutes at 94° C., followed by 30 cycles of denaturation at 94° C. for 30 seconds, annealing at 55° C. for 15 seconds, and primer extension at 68° C. for 4 minutes. The PCR products were subjected to electrophoresis in 1.5% (w/v) agarose gels in 1×TAE buffer (40 mM Tris-acetate, 1 mM EDTA), stained with a solution of ethidium bromide (1 µg/ml) and viewed using UV light.

Sequencing of Bpmp-72 from *B. pilosicoli* Strains

PCR products from six *B. pilosicoli* strains were purified using the UltraClean PCR Clean-up Kit according to the manufacturer's instructions. Sequencing of the PCR product was performed in duplicate using the AHP-98F, AHP+1890R and AHP+1012R (5'-TATCGCTTGCAGTTTGAGGAG-3') (SEQ ID NO: 33) primers. Each sequencing reaction was performed in a 10 µl volume consisting of PCR product (50 ng), primer (2 pmol), and the ABI PRISM™ Dye Terminator Cycle Sequencing Ready Reaction Mix (4 µl) (PE Applied Biosystems). Cycling conditions involved a 2 minute denaturing step at 96° C., followed by 25 cycles of denaturation at 96° C. for 10 seconds, primer annealing at 55° C. for 5 seconds, and primer extension at 60° C. for 4 minutes. Residual dye terminators were removed from the sequencing products by precipitation with 95% (v/v) ethanol containing 120 mM sodium acetate (pH 4.6), and vacuum dried. The sequencing products were analysed using an ABI 373A DNA Sequencer. Sequence results were edited, compiled and compared using SeqEd v1.0.3, Vector NTI version 6 and ClustalX.

Results

Isolation and Characterisation of Recombinant Phagemids Encoding the 72 kDa Outer-Membrane Protein in *E. coli*

Figure 2:
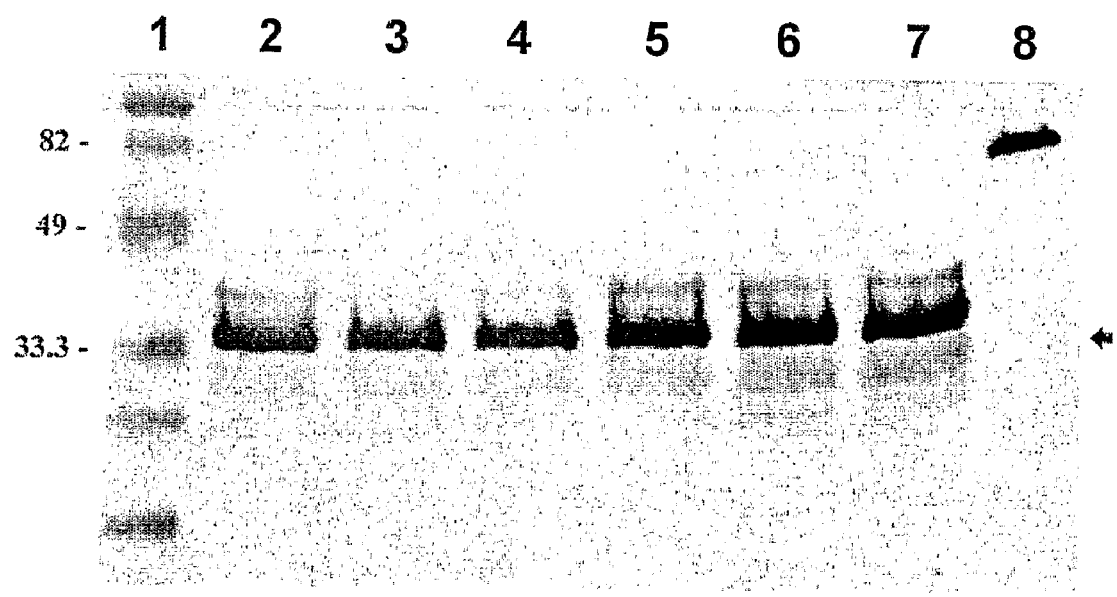
FIG. 2 Western Blot analysis of the absorbed hyper-immunised pig serum (AHPS) with the *E. coli* cells expressing the truncated 72 kDa outer-membrane protein of *B. pilosicoli*. Lane 1-molecular weight markers; lane 2-AHP1; lane 3-AHP2; lane 4-AHP3; lane 5-AHP4; lane 6-AHP5; lane 7-AHP6; lane 8-*B. pilosicoli* 95/1000 outer membrane protein. The 34 kDa truncated protein is indicated with the arrow.

Serum from a pig hyperimmunised with a *B. pilosicoli* bacterin was absorbed with *Brachyspira* spp. (except *B. pilosicoli*) whole cells and *E. coli* whole cells, as described above. Western blot analysis of the absorbed serum (AHPS) against outer envelope extracts of *B. pilosicoli* showed that AHP reacted predominantly with a protein with an apparent molecular weight of 72 kDa (FIG. 1). Screening of the *B. pilosicoli* lambda ZAP genomic library produced six clones, designated AHP1-6. These clones all produced a common protein with an apparent molecular weight of 34 kDa, all of which reacted strongly with AHPS (FIG. 2). Sequencing of one clone identified a 783 base pair partial ORF with a coding capacity of 29.4 kDa. It is proposed that this partial ORF encodes the carboxy-terminal portion of the 72 kDa outer-membrane protein of *B. pilosicoli*.

Sequence Analysis of the Open Reading Frame

Motifs and Conserved Domains

Sequencing of the AHP1 plasmid using the primers listed in Table 2 revealed a 1009 base pair insert of *B. pilosicoli* genomic DNA. Sequence analysis of the insert DNA revealed a potential partial ORF of 783 base pair from bases 1 to 783, with a putative ATG start codon and a TAA stop codon (FIG. 3). Further cloning and sequencing of the remaining gene revealed the coding sequence of Bpmp-72 to be 1,689 nucleotides in size. A potential Shine-Dalgarno ribosome binding site (AGGAG), and putative −10 (TAATAT) and −35 (TTGAAA) promoter regions were identified upstream from the ATG start codon. The gene sequence encoding the 72 kDa outer-membrane protein was designated outer-membrane protein of 72 kDa molecular weight (Bpmp-72).

The translated polypeptide consisted of 563 amino acid (aa) residues with a predicted molecular weight of 62.1 kDa. The deduced size differed significantly from those seen in the Western blots of the native Bpmp-72 protein. The difference in molecular weight between the hypothetical coding capacity of Bpmp-72 and the native Bpmp-72 outer-membrane protein is probably due to post-translational modifications such as acylation, methylation, acetylation, phosphorylation and sulphation. Analysis of the amino acid sequence revealed the presence of a 118 residue region at the C-terminus of the translated polypeptide which was homologous to a conserved lysine motif (LysM) domain. This domain is a widespread protein module which was originally identified in enzymes which degrade bacterial cell walls although it has since been shown to be present in many other bacterial proteins. The LysM domain is one of the most common modules in bacterial cell surface proteins. Other bacterial proteins which possess the LysM domain, such as *Staphlococci* IgG binding proteins and *E coli* intimin, are involved in bacterial pathogenesis.

Sequencing of the Bpmp-72 Gene Present in *Brachyspira* spp.

Genomic DNA from 48 strains of *B. hyodysenteriae*, 18 strains of *B. pilosicoli*, 12 strains of *B. intermedia*, 8 strains of *B. murdochii*, 4 strains of *B. innocens*, 2 strains of "*B. canis*", 2 strains of *B. alvinipulli* and 1 strain of *B. aalborgi* was amplified using the Bpmp-72-specific PCR. The Bpmp-72 gene was present in all strains of *B. pilosicoli* but was not present in any strains of *B. hyodysenteriae*, *B. intermedia*, *B. murdochii*, *B. innocens* "*B. canis*", *B. alvinipulli* or *B. aalborgi*. Six strains of *B. pilosicoli* were selected for sequencing of the Bpmp-72 gene present. Tables 3 and 4 summarises the level of homology between the Bpmp-72 genes of the *B. pilosicoli* strains.

The Bpmp-72 gene of the six *B. pilosicoli* strains showed 99.8-100% homology at the nucleotide level (Table 3). All strains posses a 1,689 bp gene which translates into a 563 amino acid protein. The high level of homology between the different strains of *B. pilosicoli* suggests that Bpmp-72 may be a highly conserved locus within the species.

TABLE 3

|  | P43/6/78$^T$ | 1404/6A | 95/1000 | 3295/60B | Wand 9J-0438 | Q98.0078.38 |
|---|---|---|---|---|---|---|
| P43/6/78$^T$ | 100 | | | | | |
| 1404/6A | 99.6 | 100 | | | | |
| 95/1000 | 99.5 | 99.5 | 100 | | | |
| 3295/60B | 99.4 | 99.3 | 99.3 | 100 | | |
| Wand 9J-0438 | 99.5 | 99.5 | 99.4 | 99.2 | 100 | |
| Q98.0078.38 | 99.1 | 99.0 | 99.1 | 98.9 | 99.1 | 100 |

The Bpmp-72 gene of the six *B. pilosicoli* strains showed 99.3-100% at the amino acid level (Table 4). All strains posses a 1,689 base pair gene which translates into a 563 amino acid protein. The high level of homology between the different strains of *B. pilosicoli* suggests that Bpmp-72 may be a highly conserved locus within the species.

TABLE 4

|  | P43/6/78$^T$ | 1404/6A | 95/1000 | 3295/60B | Wand 9J-0438 | Q98.0078.38 |
|---|---|---|---|---|---|---|
| P43/6/78$^T$ | 100 | | | | | |
| 1404/6A | 100 | 100 | | | | |
| 95/1000 | 100 | 100 | 100 | | | |
| 3295/60B | 99.8 | 99.8 | 99.8 | 100 | | |
| Wand 9J-0438 | 99.6 | 99.6 | 99.6 | 99.5 | 100 | |
| Q98.0078.38 | 99.5 | 99.5 | 99.5 | 99.3 | 100 | 100 |

EXAMPLE 2

Cloning, Expression and Purification of the Recombinant 72 kDa Outer-Envelope Protein (Bpmp-72) of *Brachyspira pilosicoli*

Method

Plasmid Extraction

*Escherichia coli* JM109 clones harbouring the pTrcHis plasmid (Invitrogen) were streaked out from glycerol stock storage onto Luria-Bertani (LB) agar plates supplemented with ampicillin (100 mg/l) and incubated at 37° C. for 16 hours. A single colony was used to inoculate LB broth (10 ml) supplemented with ampicillin (100 mg/l) and the broth culture was incubated at 37° C. for 12 hours with shaking. The entire overnight culture was centrifuged at 5,000×g for 10 minutes and the plasmid contained in the cells extracted using the QIAprep Spin Miniprep Kit (Qiagen) according to the manufacturer's instructions. The purified plasmid was quantified using a Dynaquant DNA fluorometer (Hoefer) and the DNA concentration adjusted to 100 µg/ml by dilution with TE buffer. The purified pTrcHis plasmid was stored at −20° C.

Vector Preparation

Purified pTrcHis plasmid (1 µg) was digested at 37° C. overnight in a total volume of 100 µl containing 5 U of EcoR1 (New England Biolabs) and 5 U of Xho1 (New England Biolabs) in 100 mM Tris-HCl (pH 7.5), 50 mM NaCl, 10 mM $MgCl_2$, 1 mM DTT and 100 µg/ml BSA. The restricted vector was verified by electrophoresis of the digestion reaction (2 µl) through a 1% (w/v) agarose gel in 1×TAE buffer at 90V for 1 h. The electrophoresed DNA was stained with a solution of ethidium bromide (1 µg/ml) and viewed using ultraviolet (UV) light.

Linearised pTrcHis vector was purified using the Ultra-Clean PCR Clean-up Kit (Mo Bio Laboratories) according to the manufacturer's instructions. Purified linear vector was quantified using the fluorometer and the DNA concentration adjusted to 50 µg/ml by dilution with TE buffer. The purified restricted vector was stored at −20° C.

Insert Preparation

Primer Design

Three pairs of primers were designed to amplify different portions of the Bpmp-72 gene. The primer sequences and the resulting gene portion cloned are shown in Table 5. All primer sequences included terminal restriction enzyme sites to enable cohesive-end ligation of the resultant amplicon into the linearised pTrcHis vector. The forward primers were designed such that a terminal Xho1 restriction enzyme site was in frame with the expression cassette of pTrcHis. The reverse primers were designed such that no premature translation stop codons would be created following ligation into the EcoR1 cloning site of the pTrcHis vector. The primers were tested using Amplify 1.2 (University of Wisconsin) and the theoretical amplicon sequence was inserted into the appropriate position in the pTrcHis vector sequence. Deduced translation of the chimeric pTrcHis expression cassette was performed using Vector NTI version 6 (InforMax) to confirm that the Bpmp-72 insert would be in the correct reading frame.

Amplification of the Bpmp-72 Inserts

The Bpmp-72 insert was amplified by PCR in a 100 µl total volume using Taq DNA polymerase (Biotech International) and Pfu DNA polymerase (Promega). Briefly, the amplification mixture consisted of 1× PCR buffer (containing 1.5 mM of $MgCl_2$), 1 U of Taq DNA polymerase, 0.1 U Pfu DNA polymerase, 0.2 mM of each dNTP (Amersham Pharmacia Biotech), 0.5 µM of the appropriate primer pair (AHP-F1-Xho1/AHP-R783-EcoR1, AHP-F1-Xho1/AHP-R223-EcoR1 or AHP-F4-Xho1/AHP-R783-EcoR1), and 2.5 µl chromosomal template DNA. Chromosomal DNA was prepared by resuspending 10 µl of frozen *B. pilosicoli* strain 95/1000 (Western Australian field strain isolated from a pig) in 200 µl TE and boiling for 1 minute. The boiled cells were centrifuged at 20,000×g for 5 minutes and the supernatant collected and used as template for the PCR. Cycling conditions involved an initial template denaturation step of 5 min at 94° C., followed by 30 cycles of denaturation at 94° C. for 30 seconds, annealing at 50° C. for 15 seconds, and primer extension at 68° C. for 2 minutes. The PCR products were subjected to electrophoresis in 1.5% (w/v) agarose gels in 1× TAE buffer, stained with a solution of ethidium bromide (1 µg/ml) and viewed using UV light. After verifying the presence of the correct size PCR product, the PCR reaction was purified using the UltraClean PCR Clean-up Kit, as previously described.

Restriction Enzyme Digestion of the Bpmp-72 Inserts

Purified PCR product (50 µl) was digested in a 100 µl total volume with 1 U of EcoR1 and 1 U of Xho1 in 100 mM Tris-HCl (pH 7.5), 50 mM NaCl, 10 mM $MgCl_2$, 1 mM DTT and 100 µg/ml BSA at 37° C. overnight. The digested insert DNA was purified using the UltraClean PCR Clean-up Kit. Purified digested insert DNA was eluted from the clean-up column using TE buffer (50 µl) and was quantified using the fluorometer and the DNA concentration adjusted to 20 µg/ml by dilution with TE buffer. The purified restricted insert DNA was used immediately for vector ligation.

Ligation of the Bpmp-72 Inserts into the pTrcHis Vector

Ligation reactions were all performed in a total volume of 20 µl. Xho1/EcoR1-linearised pTrcHis (100 ng) was incubated with Xho1/EcoR1-restricted Bpmp-72 insert (20 ng) at 14° C. for 16 hours in 30 mM Tris-HCl (pH 7.8), 10 mM $MgCl_2$, 10 mM DTT and 1 mM ATP containing 1 U of T4 DNA ligase (Promega). An identical ligation reaction containing no Bpmp-72 insert DNA was also included as a vector re-circularisation negative control.

TABLE 5

| Primer Pair | Sequence (5'-3') | Product (bp) | SEQ ID NO: |
|---|---|---|---|
| AHP-F1-Xho1 | AGACTCGAGAGTACTTTAATAAAGAAAATCGTAG | 1689 | 34 |
| AHP-R783-EcoR1 | GTTGAATTCTTACTGTTGTGCTTGAGTAGTG | 1689 | 35 |
| AHP-F1-Xho1 | as above | 1227 | 34 |
| AHP-R223-EcoR1 | TAAGAATTCCTTATAAGTCTGTCTCTTCTTG | 1227 | 36 |
| AHP-F4-Xho1 | CTACTCGAGCAAGTAATAGCTAAAGGTGATG | 782 | 37 |
| AHP-R783-EcoR1 | as above | 782 | 35 |

Transformation of pTrc-Bpmp-72 Ligations into *E coli* Cells

Competent *E. coli* BL21 Star™ (DE3) pLys One Shot® (Invitrogen) cells were thawed from −80° C. storage on ice and then cells (50 µl) were transferred into ice-cold 1.5 ml microfuge tubes containing 5 µl of the overnight ligation reactions (equivalent to 25 ng of pTrcHis vector). The tubes were mixed by gently tapping the bottom of each tube on the bench and left on ice for 30 minutes. The cells were then heat-shocked by placing the tubes into a 42° C. water-bath for 45 seconds before returning the tube to ice for 2 minutes. The transformed cells were recovered in LB broth (1 ml) for 1 hour at 37° C. with gentle mixing. The recovered cells were harvested at 2,500×g for 5 minutes and the cells resuspended in fresh LB broth (50 µl). The entire volume of resuspended cells (50 µl) was spread evenly onto a LB agar plate containing ampicillin (100 mg/l) using a sterile glass rod. Plates were incubated at 37° C. for 16 hours.

Detection of pTrc-Bpmp-72 Inserts in *E. coli* by PCR

Twelve single transformant colonies for each construct were streaked onto fresh LB agar plates containing ampicillin (100 mg/l) and incubated at 37° C. for 16 hours. A single colony from each transformation event was resuspended in TE buffer (50 µl) and boiled for 1 minute. An aliquot of boiled cells (2 µl) was used as template for PCR. The amplification mixture consisted of 1× PCR buffer (containing 1.5 mM of $MgCl_2$), 1 U of Taq DNA polymerase, 0.2 mM of each dNTP, 0.5 µM of the pTrcHis-F primer (SEQ ID NO: 6) and 0.5 µM of the pTrcHis-R primer (5'-TGCCTGGCAGTTC-CCTACTCTCG-3') (SEQ ID NO:38). Cycling conditions involved an initial template denaturation step of 5 minutes at 94° C., followed by 30 cycles of denaturation at 94° C. for 30 seconds, annealing at 60° C. for 15 seconds, and a primer extension at 72° C. for 30 seconds. The PCR products were subjected to electrophoresis in 1.5% (w/v) agarose gels in 1×TAE buffer, stained with a solution of ethidium bromide (1 µg/ml) and viewed using UV light.

Verification of pTrc-Bpmp-72 Reading Frame by Direct Sequence Analysis

Two transformant clones for each construct which produced the correct sized PCR products were inoculated into LB broth (10 ml) containing ampicillin (100 mg/l) and incubated at 37° C. for 12 hours with shaking. The entire overnight cultures were centrifuged at 5,000×g for 10 minutes and the plasmid contained in the cells extracted using the QIAprep Spin Miniprep Kit as described previously. The purified plasmid was quantified using the fluorometer.

Both purified plasmids were subjected to automated direct sequencing of the pTrcHis expression cassette using the pTrcHis-F and pTrcHis-R primers. Each sequencing reaction was performed in a 10 µl volume consisting of plasmid DNA (200 ng), primer (2 pmol) and the ABI PRISM™ Dye Terminator Cycle Sequencing Ready Reaction Mix (4 µl) (PE Applied Biosystems). Cycling conditions involved a 2 minute denaturing step at 96° C., followed by 25 cycles of denaturation at 96° C. for 10 seconds and a combined primer annealing and extension step at 60° C. for 4 minutes. Residual dye terminators were removed from the sequencing products by precipitation with 95% (v/v) ethanol containing 120 mM sodium acetate (pH 4.6), and vacuum dried. The plasmids were sequenced in duplicate using each primer. Sequencing products were analysed using an ABI 373A DNA Sequencer (PE Applied Biosystems). Successfully ligated plasmids were designated pTrc-Bpmp-72 (entire protein), pTrc-Bpmp-72N (N-terminus portion) and pTrc-Bpmp-72C(C-terminus portion).

Large-Scale Expression of Recombinant $HiS_6$-Bpmp-72C

The recombinant 34 kDa C-terminal portion of Bpmp-72 was chosen for large-scale production and subsequent use as a vaccine. A single colony of pTrc-Bpmp-72C in *E. coli* BL21 was inoculated into LB broth (50 ml) in a 250 ml conical flask containing ampicillin (100 mg/l) and incubated at 37° C. for 16 hours with shaking. A 2 L conical flask containing of LB broth (1 L) supplemented with ampicillin (100 mg/l) was inoculated with the overnight culture (10 ml) and incubated at 37° C. until the optical density of the cells at 600 nm was 0.5 (approximately 3-4 hours). The culture was then induced by adding IPTG to a final concentration of 1 mM and the cells returned to 37° C. with shaking. After 5 hours of induction, the culture was transferred to 250 ml centrifuge bottles and the bottles were centrifuged at 5,000×g for 20 minutes at 4° C. The supernatant was discarded and each pellet was resuspended with 10 ml Ni-NTA denaturing lysis buffer (100 mM $NaH_2PO_4$, 10 mM Tris-HCl, 8 M urea, pH 8.0). The resuspended cells were stored at −20° C. overnight.

Large-Scale Purification of Recombinant $His_6$-Bpmp-72C

The cell suspension was removed from −20° C. storage and thawed on ice. The cell lysate was then sonicated on ice 3 times for 30 seconds with 1 minute incubation on ice between sonication rounds. The lysed cells were cleared by centrifugation at 20,000×g for 10 minutes at 4° C. and the supernatant transferred to a 15 ml column containing a 1 ml bed volume of Ni-NTA agarose resin (Qiagen). The recombinant $His_6$-tagged protein was allowed to bind to the resin for 1 hour at 4° C. with end-over-end mixing. The resin was then washed with 50 ml of Ni-NTA denaturing wash buffer (100 mM $NaH_2PO_4$, 10 mM Tris-HCl, 8 M urea, pH 6.3) before elution with 30 ml of Ni-NTA denaturing elution buffer (100 mM $NaH_2PO_4$, 10 mM Tris-HCl, 8 M urea, pH 4.5). Three 10 ml fractions of the eluate were collected and stored at 4° C. An aliquot of each eluate (30 µl) was treated with 4× sample treatment buffer (10 µl) and boiled for 5 minutes. The samples were subjected to SDS-PAGE and stained with Coomassie Brilliant Blue G250 (Sigma). The stained gel was equilibrated in distilled water for 1 hour and dried between two sheets of cellulose overnight at room temperature.

Dialysis and Lyophilisation of the Purified Recombinant $His_6$-Bpmp-72C

The eluted proteins were pooled and transferred into a hydrated dialysis tube (Spectrum) with a molecular weight cut-off (MWCO) of 3,500 Da. An aliquot of the pooled eluate (200 µl) was taken and quantified using the Biorad Protein Assay (Biorad) according to the manufacturer's instructions. The proteins were dialysed against 2 l of distilled water at 4° C. with stirring. The dialysis buffer was changed 8 times at 12-hourly intervals. The dialysed proteins were transferred from the dialysis tube into a 50 ml centrifuge tubes (40 ml maximum volume) and the tubes were placed at −80° C. overnight. Tubes were placed into a MAXI freeze-drier (Heto) and lyophilised to dryness. The lyophilised proteins were then re-hydrated with PBS to a concentration of 2 mg/ml and stored at −20° C.

Results

Construction of the Recombinant pTrc-Bpmp-72 Vectors

Table 6 shows the constructs for the expression of different portions of the Bpmp-72 protein in *E. coli*. The primer pairs used for the generation of the cloned insert are shown in Table 5. The primers amplify a defined portion of the Bpmp-72 resulting in the expression of the complete, N-terminal portion or C-terminal portion of the Bpmp-72 protein. Cloning of the various inserts into the pTrcHis expression vector produced recombinant vectors pTrc-Bpmp-72, pTrc-Bpmp-72N and pTrc-Bpmp-72C which were 6,081, 5,518 and 5,171 bp in size, respectively. Nucleotide sequencing of the pTrcHis constructs verified that the expression cassette was in the correct frame for all the constructs. The predicted translation of the pTrcHis expression cassette indicated that the recombinant $His_6$-Bpmp-72 protein (66.3 kDa), $His_6$-Bpmp-72N (46.9 kDa), $His_6$-Bpmp-72 (34.6 kDa) and the deduced amino acid sequence of the native Bpmp-72 lipoprotein (62.1 kDa) were identical. Complete plasmid maps of the pTrcHis constructs are shown in FIG. 4.

TABLE 6

| Construct name | Primer pair used | Gene portion expressed | Protein expressed (kDa) |
| --- | --- | --- | --- |
| pTrc-Bpmp-72 | AHP-F1-Xho1 AHP-R783-EcoR1 | Full protein | 66.3 |
| pTrc-Bpmp-72N | AHP-F1-Xho1 AHP-R223-EcoR1 | N-terminal portion | 46.9 |
| pTrc-Bpmp-72C | AHP-F4-Xho1 AHP-R783-EcoR1 | C-terminal portion | 34.6 |

Expression and Purification of Recombinant Bpmp-72C

Figure 5:
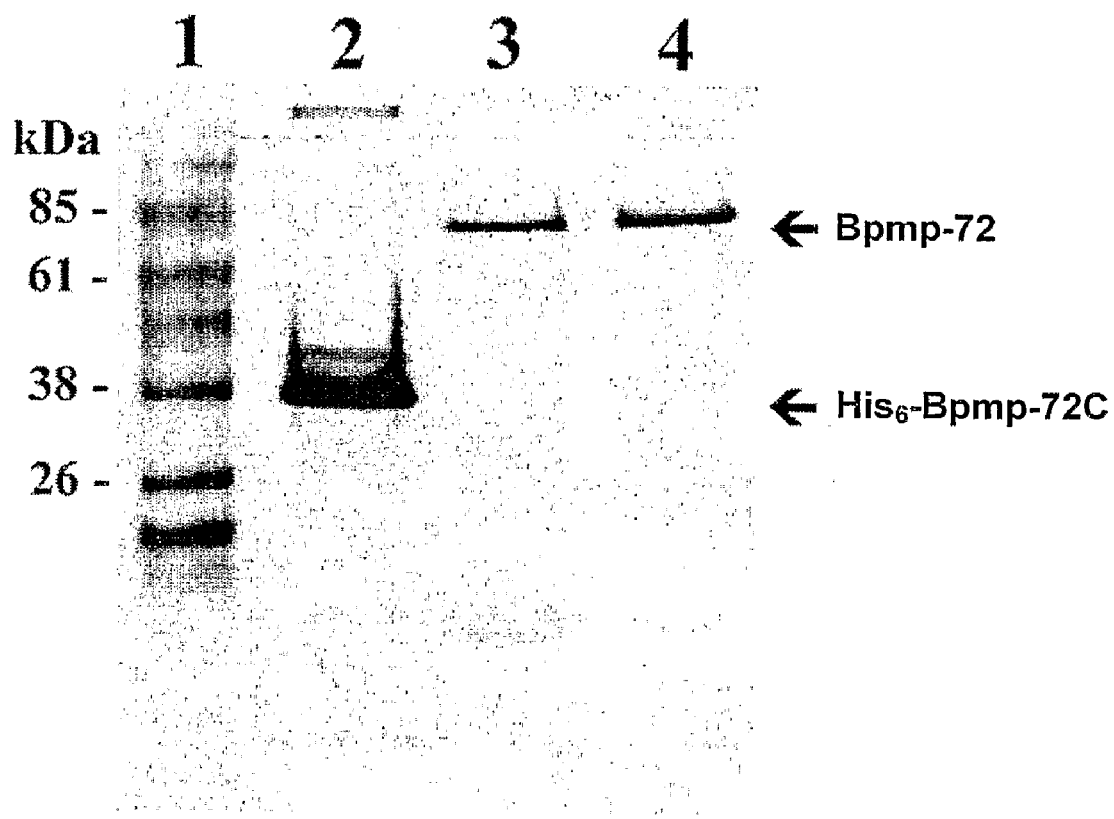
FIG. 5 Western Blot analysis of native Bpmp-72 (designated Omp-72 in the figure) and the recombinant C-terminal portion of Bpmp-72 ($His_6$-Bpmp-72C). Lane 1-molecular weight markers; lane2-purified $His_6$-Bpmp-72C; lane 3—native Bpmp-72C from *B. pilosicoli* 95/1000; lane 4—native Bpmp-72C from *B. pilosicoli* Csp1. the arrows indicate the position of the native and recombinant Bpmp-72 proteins.

Expression of the selected recombinant clone containing pTrc-Bpmp-72C was performed in large-scale to generate sufficient recombinant protein for vaccination. Recombinant Bpmp-72C protein with hexa-histidine fusion (4 kDa) produced a major protein with an apparent molecular weight of 34 kDa (FIG. 5). The AHPS used in the initial screening of the lambda bacteriophage genomic library reacted with both the native Bpmp-72 and the recombinant $His_6$-Bpmp-72C (FIG. 5).

Figure 6:
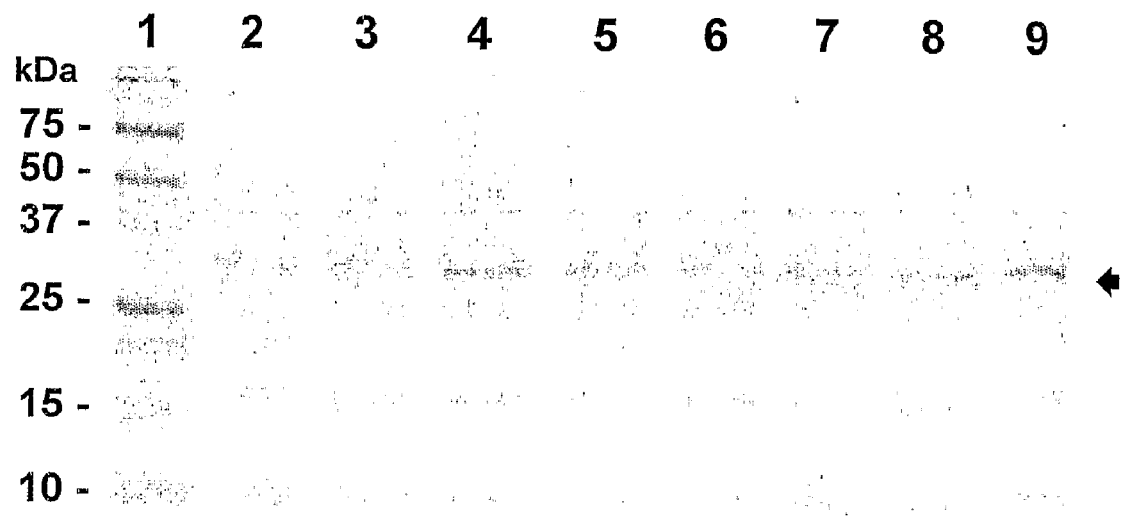
FIG. 6 SDS-PAGE analysis of different batches of recombinant $His_6$-Bpmp-72 purified using N-NTA chromatography. All batches of recombinant protein were expressed and purified using the same method. Lane 1—molecular weight markers; lane 2 to 9—purified $His_6$-Bpmp-72C batch 1-6. The recombinant $His_6$-Bpmp-72C protein is indicated with an arrow.

Purification of the $His_6$-Bpmp-72 recombinant antigen by affinity chromatography under denaturing conditions was successful. SDS-PAGE of six replicate batches of large-scale purified $His_6$-Bpmp-72C showed that the recombinant antigen was better than 90% pure and that expression of the protein was consistent (FIG. 6). Recombinant protein yields of 2 mg/L were consistently obtained using this expression protocol. Following dialysis and lyophilisation, stable recombinant $His_6$-Bpmp-72C antigen was successfully produced.

EXAMPLE 3

Vaccination of Chickens Using the Carboxy-Terminal Portion of the Recombinant 72 kDa Outer-Envelope Protein (Bpmp-72) of *Brachyspira pilosicoli*

Method

Two groups of 15 chickens were systemically and orally immunised with the recombinant 34 kDa C-terminal portion of the 72 kDa protein of *B. pilosicoli* ($His_6$-Bpmp-72C), then challenged with *B. pilosicoli*, in order to determine whether the vaccination would protect from *B. pilosicoli* colonisation. A third group of 15 unvaccinated hens were included as controls. All 45 birds were housed in individual cages in one room. The designation of the three groups were:
i) Group A: receiving no vaccination;
ii) Group B: receiving recombinant protein (100 µg) with adjuvant intramuscularly, followed 3 weeks later by 1 mg protein in solution via crop tube;
iii) Group C: receiving 1 mg recombinant protein with adjuvant intramuscularly, followed 3 weeks later by 1 mg protein in solution via crop tube.

All birds were challenged orally with a chicken strain (Csp1) of *B. pilosicoli* two weeks after the second vaccination.

Chickens and Immunisation Protocols

The recombinant 34 kDa C-terminal portion of the Bpmp-72 ($His_6$-Bpmp-72C) was emulsified with an equal volume of Freund's Incomplete adjuvant and injected intramuscularly into the pectoral muscles of the fifteen pullets (ISA Brown layer pullets: each bird about 18 weeks old and 1.5 kg body weight) in each of Groups B and C. Birds from Group B each received 100 ug of protein in a total volume of 1 ml, and birds from Group C each received 1 mg of protein in a total volume of 1 ml. Birds from Group A received no vaccination. Three weeks after the first vaccination, all birds from Groups B and C received 1 mg of protein in 2 ml phosphate buffered saline directly into the crop. Birds from Group A received no vaccination. Two weeks after the oral vaccination, all birds were given 2 ml of exponential log-phase (~$10^9$ cells/ml) *B. pilosicoli* directly into the crop. Challenge was repeated over three consecutive days. The birds were individually caged.

Sera were obtained by bleeding from the wing vein prior to the first vaccination, just prior to the second vaccination, prior to the first day of challenge, and five weeks later. The sera were tested in ELISA for antibodies to the vaccine antigen, and also in Western Blot analysis against cellular extracts of *B. pilosicoli*. Faeces from all birds were swabbed three times per week and cultured. The birds were killed five weeks after experimental infection by cervical dislocation. Small intestinal and colonic scrapings were collected at post-mortem and tested for specific immunoglobulin content by ELISA and Western blot analysis.

Spirochaetal Culture

Swabs taken from faeces were streaked onto Trypticase Soy agar plates containing 5% (v/v) defibrinated sheep blood, spectinomycin (400 µg/ml), colistin (25 µg/ml) and vancomycin (25 µg/ml). These plates were incubated at 37° C. in an aerobic environment for seven days. Spirochaetes were identified as *B. pilosicoli* on the basis of weak beta-haemolysis and microscopic morphology. A subset of isolates were subcultured and confirmed as *B. pilosicoli* using a species-specific PCR.

ELISA (Serum)

Wells of Microtitre plates (Immulon 4HBX, Dynex) were coated with 100 µl purified $His_6$-Bpmp-72C (1 µg/ml) in carbonate buffer (pH 9.6) and incubated at 4° C. overnight. Plates were blocked with 150 µl of PBS-BSA (1% w/v) for 1 hour at room temperature with mixing and then washed three times with 150 µl of PBST (0.05% v/v).

Chicken sera was diluted 200-fold in 100 µl of PBST-BSA (0.1% w/v) and incubated at room temperature for 2 hours with mixing. Plates were washed (as above) before adding 100 µl of goat anti-chicken IgG (whole molecule)-HRP diluted 80,000-fold in PBST. After incubating for 1 hour at room temperature, the plates were washed and 100 µl of TMB substrate added. Colour development was allowed to occur for 10 minutes at room temperature before being stopped with the addition of 50 µl of 1 M sulphuric acid. The optical density of each well was read at 450 nm.

ELISA (Mucosal)

Scrapings were taken from a 15 $cm^2$ section of the small intestine and the colon. The scrapings were re-suspended in 1 ml of PBS containing 1% (w/v) BSA, 2 mM PMSF, 1 mM EDTA and 0.2% (w/v) sodium azide. Suspensions were mixed thoroughly and centrifuged at 20,000×g for 10 minutes. The supernatant was removed, diluted 2-fold with PBST, and 100 µl used for ELISA. The ELISA was performed as for the serum ELISA.

Western Blot Analysis

An aliquot of sonicated and cleared *B. pilosicoli* cell suspension (50 mg) was loaded into a 7 cm preparative well, electrophoresed through a 12.5% (w/v) SDS-PAGE gel, and electro-transferred to nitrocellulose membrane. The membrane was blocked with TBS-skim milk (5% w/v) and assembled into the multi-probe apparatus (Biorad). The wells were incubated with 100 μl of diluted pooled chicken serum (200-fold) or mucosal supernatant (2-fold) for 2 hours at room temperature. The wells were washed three times with TBST (0.1% v/v) before incubating with 100 μl of goat anti-chicken IgG (whole molecule)-HRP (10,000-fold) for 1 hour at room temperature. The membrane was removed from the apparatus and washed three times with TBST. Colour development occurred in 10 ml of DAB solution (5 mg/ml, 0.0003% v/v hydrogen peroxide, TBS) and the membrane was washed with tap water when sufficient development had occurred. The membrane was dried and scanned for presentation.

Results

Serological Response to the Vaccination

Figure 7:
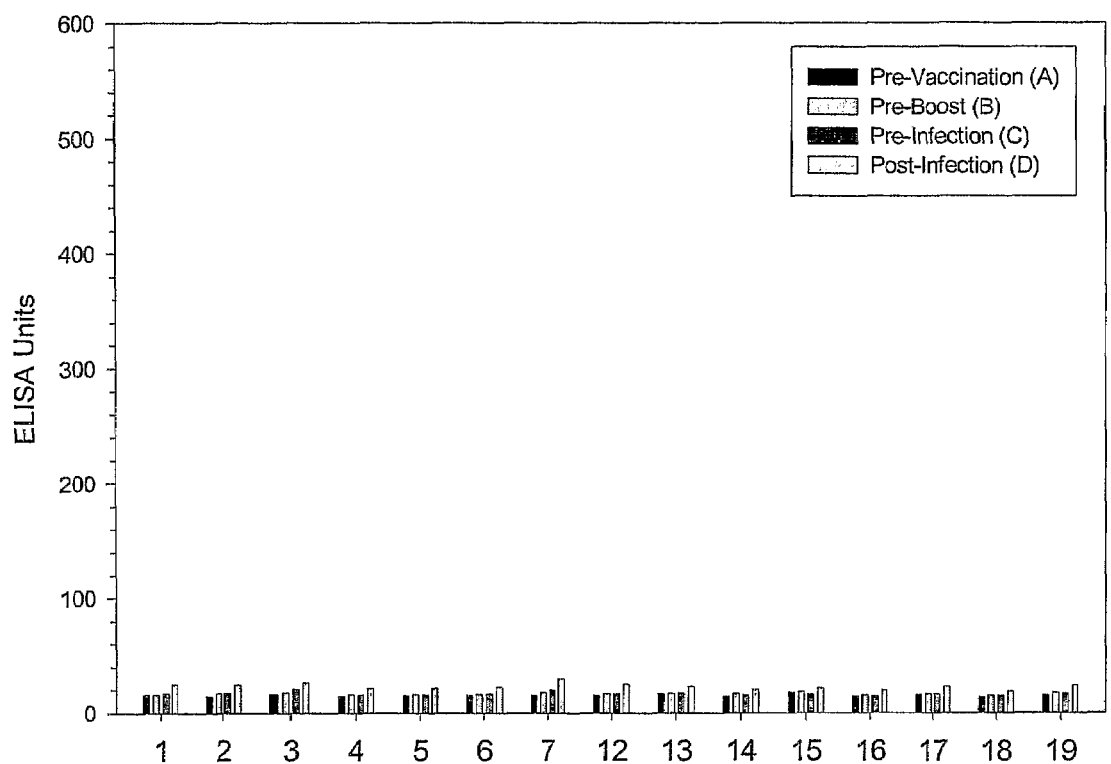
FIG. 7 Systemic antibody titres (ELISA) of the non-vaccinated chickens against recombinant $His_6$-Bpmp-72C before and after challenge with *B. pilosicoli*. Circulating antibodies were detected by ELISA using purified $His_6$-Bpmp-72C as the coating antigen.
Figure 8:
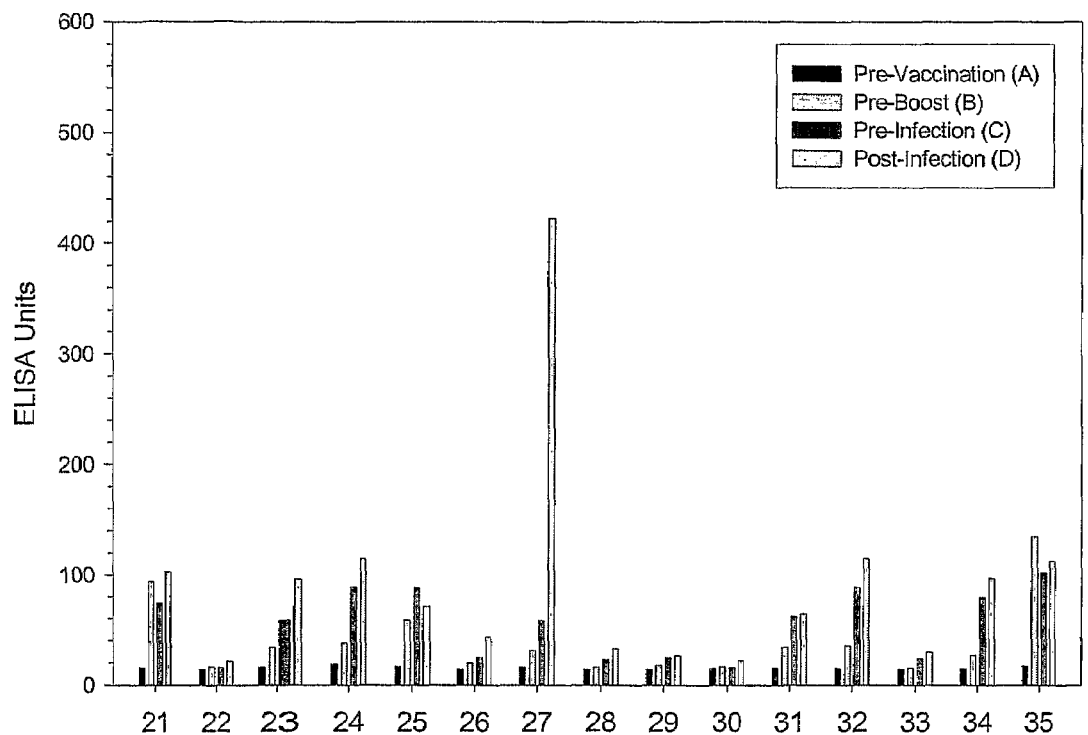
FIG. 8 Systemic antibody titres (ELISA) following vaccination of chickens with recombinant $His_6$-Bpmp-72C, and following challenge with *B. pilosicoli*. All birds were given 100 µg of protein intramuscularly followed by 1 mg oral boost. Circulating antibodies were detected by ELISA using purified $His_6$-Bpmp-72C as the coating antigen.
Figure 9:
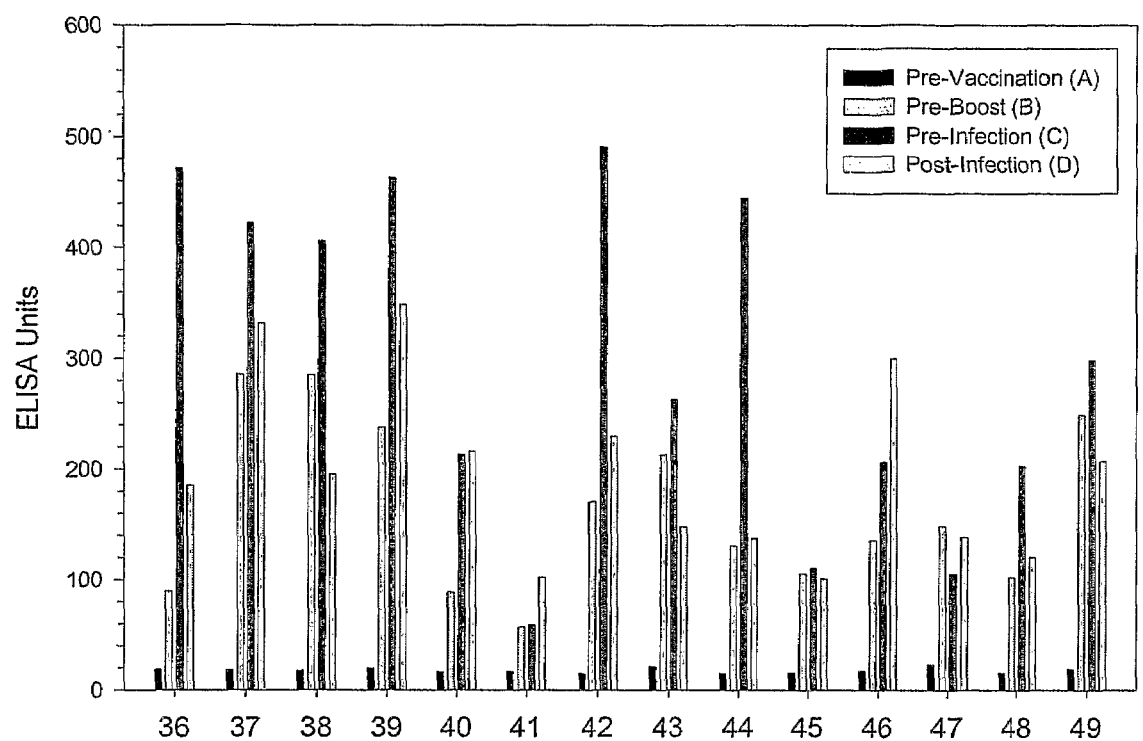
FIG. 9 Systemic antibody titres (ELISA) following vaccination of chickens with recombinant $His_6$-Bpmp-72C, and following challenge with *B. pilosicoli*. All birds were given 1 mg of protein intramuscularly followed by 1 mg oral boost. Circulating antibodies were detected by ELISA using purified $His_6$-Bpmp-72C as the coating antigen.

The systemic serological (ELISA) response of the chickens are shown in FIGS. 7-9. Control birds (Group A) did not have circulating antibody, and none developed after experimental infection (FIG. 7). The lack of a boost to circulating antibody after experimental infection was also seen in most but not all of the vaccinated birds (FIG. 8 and FIG. 9). Six of the birds vaccinated with 100 μg of protein (Group B) showed a modest primary response, with the remaining birds showing a poor response to the vaccine (FIG. 8). In contrast, good primary systemic responses were seen in eleven birds vaccinated with 1 mg of protein (Group C), with the remaining four birds from this group showing only a moderate response to the vaccination. All but three of these birds showed an increased response following the oral boost (FIG. 9).

Figure 10:
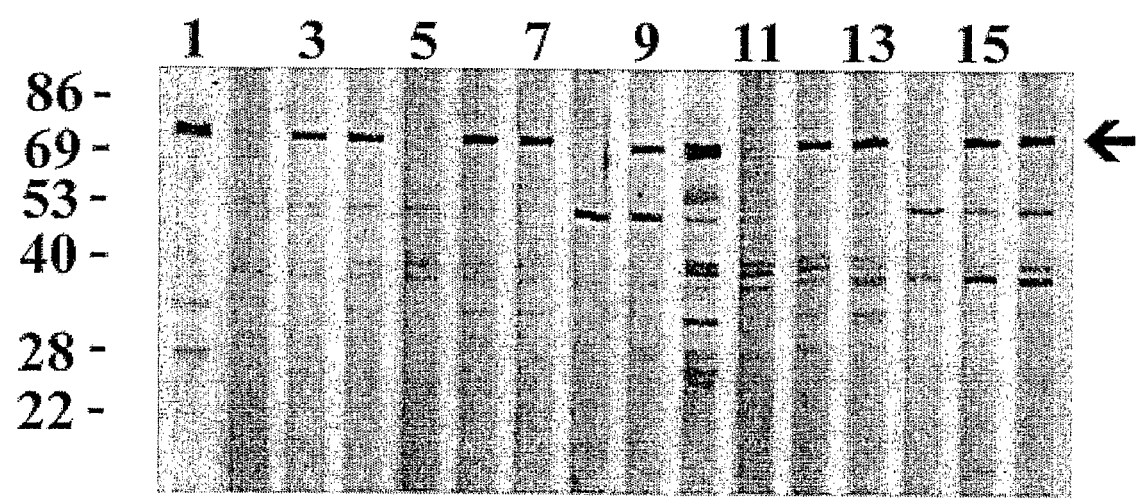
FIG. 10 Western Blot analysis of pooled serum from chickens vaccinated with 100 µg of recombinant $His_6$-Bpmp-72C intramuscularly followed by 1 mg protein orally. Serum from three chickens were pooled for each sampling time. The antigen used was a whole-cell extract of the *B. pilosicoli* strain used for challenge. Lane 1-vaccinated chicken from experiment A1 (positive control); lanes 2-4—chickens 21-23; lanes 5-7—chickens 24-26; lanes 8-1—chickens 27-29; lanes 11-13—chickens 30-32; lanes 14-16—chickens 33-35. Each triplicate includes serum taken pre-vaccination, pre-challenge and post challenge, consecutively. Molecular weight markers are shown in kDa. The native 72 kDa protein of *B. pilosicoli* is indicated with the arrow.
Figure 11:
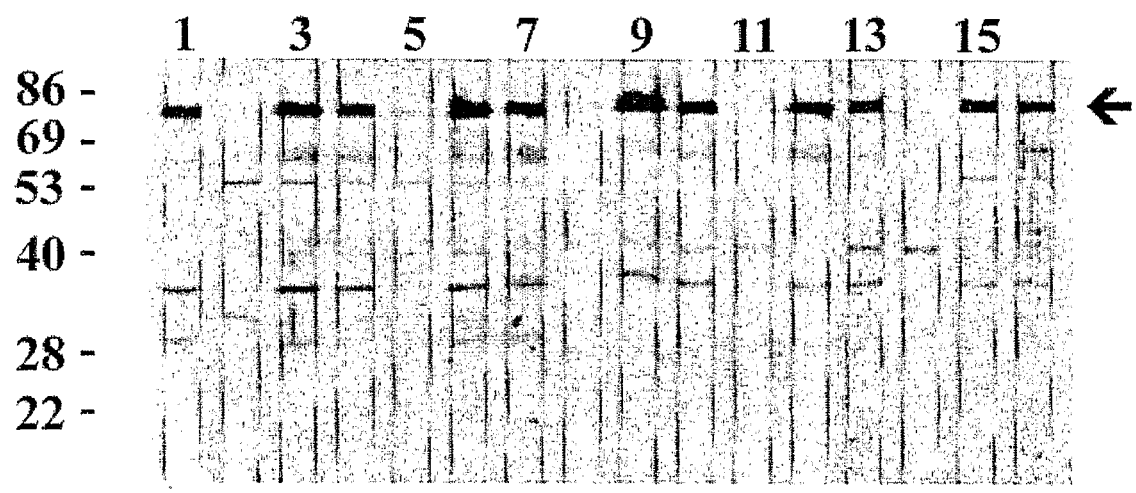
FIG. 11 Western Blot analysis of pooled serum from chickens vaccinated with 1 mg of recombinant $His_6$-Bpmp-72C intramuscularly followed by 1 mg protein orally. Serum from three chickens were pooled for each sampling time. The antigen used was a whole-cell extract of the *B. pilosicoli* strain used for challenge. Lane 1, vaccinated chicken from experiment A1 (positive control); lanes 2-4, chickens 36-38; lanes 5-7, chickens 39-41; lanes 8-10, chickens 42-44; lanes 11-13, chickens 45-47; lanes 14-16, chickens 48-50. Each triplicate includes serum taken pre-vaccination, pre-challenge and post-challenge, consecutively. Molecular weight markers are shown in kDa. The native 72 kDa protein (Bpmp-72) of *B. pilosicoli* is indicated with the arrow.

The Western blot analysis of the vaccinated chickens against the *B. pilosicoli* extract are shown in FIGS. 10 and 11. Five pools of sera, each pool from three birds, are shown for each group. The Western blots show the specificity of these responses for the native 72 kDa protein (despite vaccination with a 34 kDa subunit), and show a tendency for the Group C birds (1 mg) to have a stronger response than the group B birds (100 μg).

Figure 12:
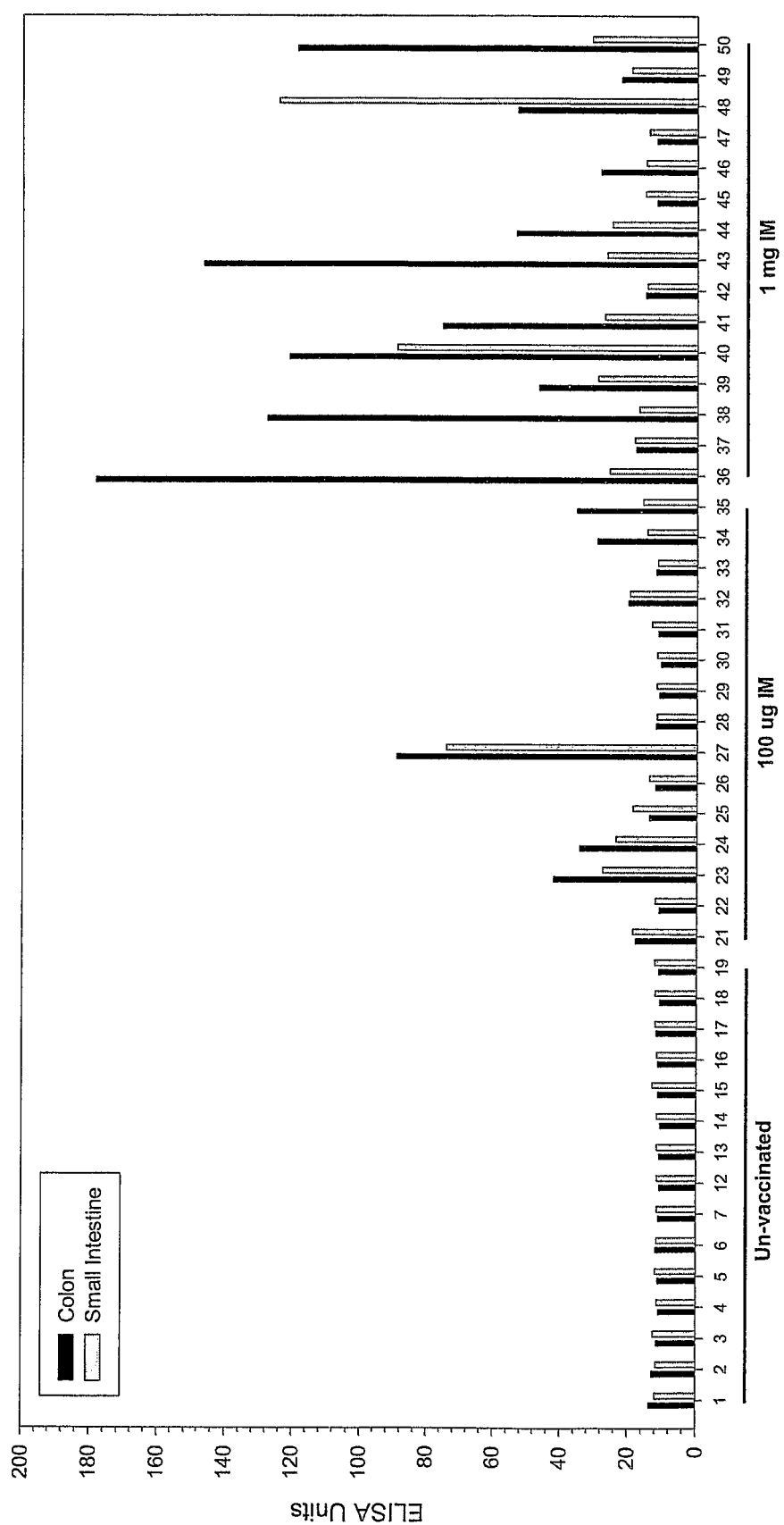
FIG. 12 Mucosal antibody titres (ELISA) at the small intestine and colon following vaccination of chickens with recombinant $His_6$-Bpmp-72C, and following challenge with *B. pilosicoli*. Birds 1-19 were not vaccinated, birds 21-35 were given 100 µg protein intramuscularly followed by 1 mg protein orally, and birds 36-50 were given 1 mg of protein intramuscularly followed by 1 mg orally. Circulating antibodies were detected by ELISA using purified $His_6$-Bpmp-72C as the coating antigen.

The mucosal ELISA response of the chickens to the vaccination and challenge (samples collected post-mortem) is shown in FIG. 12. The control birds did not show any local responses, despite being infected. Only one of the birds (number 27) from the 100 μg vaccination group (Group B) showed good local antibody response in both the small intestine and the colon. Four other birds (numbers 23, 24, 34 and 35) from this group also showed a moderate local response in the colon. Two birds (number 40 and 48) from the 1 mg vaccination group (Group C) showed good local response in the small intestine, whereas six of the birds (numbers 36, 38, 40, 41, 43 and 50) showed good local response in the colon.

Figure 13:
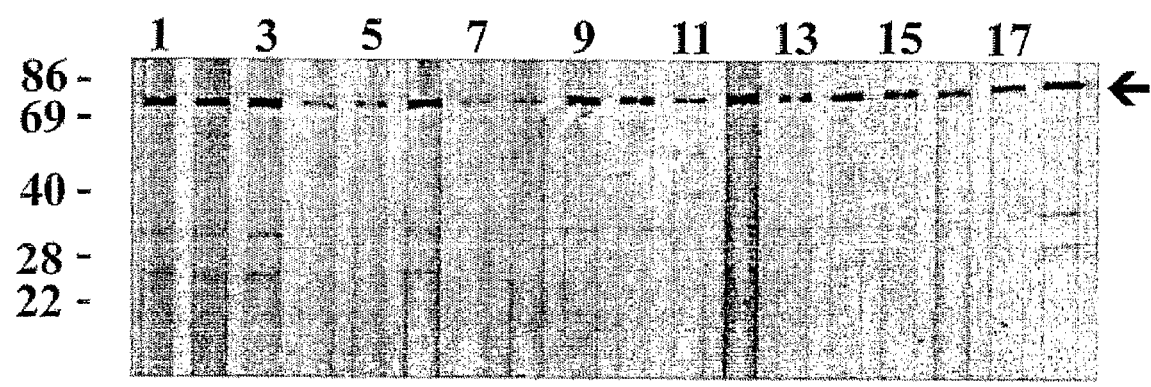
FIG. 13 Western Blot analysis of mucosal antibodies from chickens vaccinated with recombinant $His_6$-Bpmp-72C and challenged with *B. pilosicoli*. The antigen used was a whole-cell extract of the *B. pilosicoli* strain used for challenge. Lanes 1-3, small intestine antibodies; and lanes 4-17, colonic antibodies: lane 1, chicken 27; lane 2, chicken 40; lane 3, chicken 48; lanes 4-5, chickens 23-24; lane 6, chicken 27; lanes 7-9, chicken 34-36; lanes 10-13, chickens 38-41; lanes 14-15, chickens 43-44; lane 16, chicken 48; lane 17, chicken 50; lane 18, vaccinated chicken from experiment A1 (positive control). Chickens 21-35 were given 100 µg protein intramuscularly followed by 1 mg protein orally. Chickens 36-50 were given 1 mg protein intramuscularly followed by 1 mg protein orally. Molecular weight markers are shown in kDa. The native 72 kDa protein (Bpmp-72) of *B. pilosicoli* is indicated with the arrow.

Western blot analysis of the mucosal extract from the birds having higher titres of mucosal antibodies are shown in FIG. 13. The local antibody response of all the birds was against the native 72 kDa protein. These results indicate that an oral vaccination at the crop (plus a subsequent experimental challenge) is able to induce a local response further down the gastrointestinal tract. However, the success of the oral vaccination in inducing a detectable local response in the colon (and small intestine) is inconsistent.

Protection Against *B. pilosicoli* Colonisation

The summarised results of faecal culture for *B. pilosicoli* in the three groups of birds are shown in Table 7. The results for individual birds in the three groups are presented in Tables 8-10, respectively. All isolates that were sub-cultured were confirmed to be *B. pilosicoli* by a species-specific PCR targeting the 16S rRNA gene.

TABLE 7

| Days post infection | Group A (%) | Group B (%) | Group C (%) |
|---|---|---|---|
| 0 | 0 | 0 | 0 |
|   | (0/15) | (0/15) | (0/15) |
| 7 | 33 | 7 | 13 |
|   | (5/15) | (1/15) | (2/15) |
| 9 | 80 | 7 | 0 |
|   | (12/15) | (1/15) | (0/15) |
| 11 | 40 | 7 | 7 |
|   | (6/15) | (1/15) | (1/15) |
| 14 | 47 | 13 | 7 |
|   | (7/15) | (2/15) | (1/15) |
| 18 | 27 | 13 | 13 |
|   | (4/15) | (2/15) | (2/15) |
| 21 | 33 | 0 | 7 |
|   | (5/15) | (0/15) | (1/15) |
| 23 | 33 | 27 | 20 |
|   | (5/15) | (4/15) | (3/15) |
| 25 | 60 | 27 | 40 |
|   | (9/15) | (4/15) | (6/15) |
| 28 | 60 | 27 | 20 |
|   | (9/15) | (4/15) | (3/15) |
| 30 | 40 | 60 | 33 |
|   | (6/15) | (9/15) | (5/15) |
| Cumulative total | 45 | 19 | 16 |
|   | (68/150) | (28/150) | (24/150) |

By nine days post-infection (pi), the control group had developed an 80% colonisation rate, compared to 7% and 0% in the two vaccinated groups (Table 6). Subsequently, the colonisation rate in the control group declined, although it remained at an average rate of 45% over the 30 day period. In contrast, the colonisation rates in both vaccinated groups tended to increase with time, with a maximum colonisation rate of 60% in group B at day 30 post infection, and 40% in group C at day 25 post infection. Colonisation rates in the three groups were similar at 30 days post infection. Nevertheless, over the whole period, the colonisation in the control group was highly significantly greater than that in both vaccinated groups.

Table 8 shows individual colonisation results for the non-vaccinated chickens after oral challenge with *B. pilosicoli*. Colonisation was determined by culture of faecal swabs. The (−) symbol represents culture negative and (+) represents culture positive. Table 9 show individual colonisation results for the vaccinated chickens (100 μg intramuscularly plus 1 mg orally) after oral challenge with *B. pilosicioli*. Colonisation was determined by culture of faecal swabs. The (−) symbol represents culture negative and (+) represents culture positive. Table 10 show individual colonisation results for the vaccinated chickens (1 mg intramuscularly plus 1 mg orally) after oral challenge with *B. pilosicoli*. Colonisation was determined by culture of faecal swabs. The (−) symbol represents culture negative and (+) represents culture positive.

All 15 of the control birds became colonised, and that positive swabs were obtained on between 3 and 6 samplings over the experimental period (mean of 4.53 sampling days, of a possible 11).

Results for Group B showed 14 birds were colonised at some point, with between 1 and 3 samplings being positive (mean of 1.87 sampling days). In Group C, 14 birds were colonised at some point, with between 1 and 5 samplings being positive (mean of 1.6 samplings positive). These results emphasise that the total extent of the infection in the vaccinated birds was less than in the control birds, and that both vaccine regimens produced similar results in relation to protection from colonisation.

When comparing the systemic or colonic antibody responses in individual birds in relation to colonisation, no consistent picture emerges. The control birds produced little local or systemic antibody response to infection. Considering the 4 birds in group B with >2 days colonisation (numbers 21, 24, 29 and 30), their antibody titres were no lower than the other birds in this group that were colonised for less time. The bird that did not become colonised (number 26) had antibody titres similar to the others in the group. In contrast, in group C, the three birds with >2 days colonisation (numbers 37, 46 and 49) did have a poor colonic antibody response. Of these, bird 37 had a good systemic antibody response, but birds 46 and 49 did not. The bird that was not colonised (number 40) had a moderate systemic antibody response, but a good colonic response. In this vaccination group there was a tendency for higher colonic antibody titres to be found in the birds with less colonisation.

Overall, this experiment provides evidence that the vaccination protocols can induce specific circulating and colonic antibody titres against Bpmp-72. In this respect, intramuscular vaccination with 1 mg of protein gave a better response than using 100 μg. Both vaccination protocols also clearly delayed colonisation with *B. pilosicoli*, and also reduced the total duration and number of birds that were colonised (particularly compared to the peak of infection in the control birds at 9 days post infection). Had the high rate of colonisation been maintained in the control birds, this difference may have been further emphasised. These results provide a strong basis to suggest that Bpmp-72 could be developed as an effective means of protecting chickens, as well as other animal species including pigs, dogs and human beings from being colonised by *B. pilosicoli*.

TABLE 8

| Days post infection | 0 | 7 | 9 | 11 | 14 | 18 | 21 | 23 | 25 | 28 | 30 | Total Positive |
|---|---|---|---|---|---|---|---|---|---|---|---|---|
| 1 | − | − | − | − | + | + | − | + | + | + | − | 5 |
| 2 | − | + | + | − | + | − | − | + | + | − | − | 5 |
| 3 | − | − | + | + | + | − | − | − | + | + | + | 6 |
| 4 | − | − | + | + | − | − | − | + | − | + | + | 5 |
| 5 | − | − | − | + | + | + | − | − | − | + | + | 5 |
| 6 | − | + | − | + | − | − | + | − | − | − | − | 3 |
| 7 | − | − | + | − | − | − | − | + | − | − | + | 3 |
| 12 | − | + | + | − | − | − | − | − | − | − | + | 3 |
| 13 | − | − | + | − | − | + | + | − | + | − | − | 4 |
| 14 | − | + | + | − | + | − | + | − | + | + | − | 6 |
| 15 | − | − | + | + | − | − | + | − | + | + | + | 6 |
| 16 | − | − | + | − | − | − | − | + | + | + | − | 4 |
| 17 | − | − | + | − | − | − | + | + | − | + | − | 4 |

TABLE 8-continued

| Days post infection | 0 | 7 | 9 | 11 | 14 | 18 | 21 | 23 | 25 | 28 | 30 | Total Positive |
|---|---|---|---|---|---|---|---|---|---|---|---|---|
| 18 | − | − | + | + | + | − | − | − | + | − | − | 4 |
| 19 | − | + | + | − | + | + | − | − | − | + | − | 5 |
| Total Positive | 0 | 5 | 12 | 6 | 7 | 4 | 5 | 5 | 9 | 9 | 6 | 68 |

TABLE 9

| Days post infection | 0 | 7 | 9 | 11 | 14 | 18 | 21 | 23 | 25 | 28 | 30 | Total Positive |
|---|---|---|---|---|---|---|---|---|---|---|---|---|
| 21 | − | − | − | − | − | − | + | − | + | + | − | 3 |
| 22 | − | − | − | − | − | + | − | − | − | − | + | 2 |
| 23 | − | − | − | − | − | − | − | − | − | + | + | 2 |
| 24 | − | − | − | − | − | + | − | + | − | − | + | 3 |
| 25 | − | − | − | − | − | − | − | − | − | − | + | 1 |
| 26 | − | − | − | − | − | − | − | − | − | − | − | 0 |
| 27 | − | − | − | − | − | − | − | − | − | − | + | 1 |
| 28 | − | − | − | − | − | − | − | − | + | − | + | 2 |
| 29 | − | − | − | − | − | − | − | + | + | − | + | 3 |
| 30 | − | − | − | − | + | − | − | − | − | + | + | 3 |
| 31 | − | − | − | + | − | − | − | − | − | − | − | 1 |
| 32 | − | + | − | − | − | − | − | − | − | − | − | 1 |
| 33 | − | − | − | − | − | − | − | + | − | + | − | 2 |
| 34 | − | − | − | − | + | − | − | − | + | − | − | 2 |
| 35 | − | − | + | − | − | − | − | − | + | − | − | 2 |
| Total Positive | 0 | 1 | 1 | 1 | 2 | 2 | 0 | 4 | 4 | 4 | 9 | 28 |

TABLE 10

| Days post infection | 0 | 7 | 9 | 11 | 14 | 18 | 21 | 23 | 25 | 28 | 30 | Total Positive |
|---|---|---|---|---|---|---|---|---|---|---|---|---|
| 36 | − | − | − | − | − | − | − | + | + | − | − | 2 |
| 37 | − | + | − | − | − | + | − | + | + | − | + | 5 |
| 38 | − | − | − | − | + | − | − | − | + | − | − | 2 |
| 39 | − | − | − | − | − | − | − | − | − | + | − | 1 |
| 40 | − | − | − | − | − | − | − | − | − | − | − | 0 |
| 41 | − | − | − | − | − | + | − | − | − | − | − | 1 |
| 42 | − | − | − | − | − | − | − | − | + | − | − | 1 |
| 43 | − | − | − | − | − | − | + | − | − | − | − | 1 |
| 44 | − | − | − | − | − | − | − | − | − | − | + | 1 |
| 45 | − | − | − | − | − | − | − | − | − | − | + | 1 |
| 46 | − | − | − | + | − | − | − | − | + | + | − | 3 |
| 47 | − | − | − | − | − | − | − | − | + | − | − | 1 |
| 48 | − | − | − | − | − | − | − | + | − | − | − | 1 |
| 49 | − | + | − | − | − | + | + | − | − | − | − | 3 |
| 50 | − | − | − | − | − | − | − | − | − | − | + | 1 |
| Total Positive | 0 | 2 | 0 | 1 | 1 | 2 | 2 | 3 | 6 | 3 | 4 | 24 |

The claims defining the invention are as follows:

1. An isolated polypeptide consisting of an amino acid sequence corresponding to the 34 kDa C-terminal portion of SEQ ID NO:2.

2. A method of treating a disease associated with a *Brachyspira* species, the method comprising administering to an animal an effective amount of (i) a polypeptide consisting of the amino acid sequence corresponding to the 34 kDa C-terminal portion of SEQ ID NO:2 or (ii) the polypeptide of (i) together with an adjuvant.

3. The method of treating a disease according to claim 2 wherein the disease is intestinal spirochaetosis.

4. The method according to claim 2 wherein the animal is selected from the group consisting of: pigs, chickens, dogs, horses, cattle, sheep, fish, and humans.

5. A composition comprising a carrier and an immunogen wherein said immunogen is a polypeptide according to claim 1.

6. The method of claim 2, wherein the *Brachyspira* species is *Brachyspira pilosicoli*.

7. A method for treatment of infection with a *Brachyspira* species, the method comprising administering a therapeutically effective amount of a polypeptide consisting of an amino acid sequence corresponding to the 34 kDa C-terminal portion of SEQ ID NO:2.

8. The method of claim 7, wherein the *Brachyspira* species is *Brachyspira pilosicoli*.

* * * * *